(12) United States Patent
Dreno et al.

(10) Patent No.: US 11,351,201 B2
(45) Date of Patent: Jun. 7, 2022

(54) BANDAGE CONTAINING FOETAL FIBROBLASTS AND KERATINOCYTES

(71) Applicants: Universite De Nantes, Nantes (FR); Chu Nantes, Nantes (FR)

(72) Inventors: Brigitte Dreno, Nantes (FR); Thomas Zuliani, Nantes (FR); Soraya Saiagh, Le Pellerin (FR)

(73) Assignees: Universite De Nantes, Nantes (FR); Chu Nantes, Nantes (FR)

( * ) Notice: Subject to any disclaimer, the term of this patent is extended or adjusted under 35 U.S.C. 154(b) by 198 days.

(21) Appl. No.: 14/651,887

(22) PCT Filed: Dec. 12, 2013

(86) PCT No.: PCT/EP2013/076438
§ 371 (c)(1),
(2) Date: Jun. 12, 2015

(87) PCT Pub. No.: WO2014/090961
PCT Pub. Date: Jun. 19, 2014

(65) Prior Publication Data
US 2015/0320804 A1 Nov. 12, 2015

(30) Foreign Application Priority Data

Dec. 12, 2012 (FR) ...................................... 1261953

(51) Int. Cl.
| | |
|---|---|
| A61K 35/36 | (2015.01) |
| A61L 15/32 | (2006.01) |
| A61L 15/40 | (2006.01) |
| A61K 35/33 | (2015.01) |
| A61L 15/44 | (2006.01) |
| A61K 35/54 | (2015.01) |

(52) U.S. Cl.
CPC .............. *A61K 35/36* (2013.01); *A61K 35/33* (2013.01); *A61K 35/54* (2013.01); *A61L 15/32* (2013.01); *A61L 15/325* (2013.01); *A61L 15/40* (2013.01); *A61L 15/44* (2013.01); *A61L 2300/412* (2013.01); *A61L 2300/45* (2013.01); *A61L 2300/64* (2013.01)

(58) Field of Classification Search
CPC .......... A61K 35/36; A61K 35/54; A61L 15/44
See application file for complete search history.

(56) References Cited

U.S. PATENT DOCUMENTS

| | | | |
|---|---|---|---|
| 2002/0048563 A1 | 4/2002 | Baetge et al. | |
| 2003/0165482 A1 | 9/2003 | Rolland et al. | |
| 2003/0175256 A1* | 9/2003 | Laurent-Applegate | ...................... A61K 35/36 424/93.21 |
| 2008/0193507 A1* | 8/2008 | Kemp | ..................... A61K 35/34 424/443 |

FOREIGN PATENT DOCUMENTS

| | | |
|---|---|---|
| JP | 2004121819 A | 4/2004 |
| WO | 96/33750 A1 | 10/1996 |
| WO | 03/068287 A1 | 8/2003 |
| WO | 2012/038923 A1 | 3/2012 |

OTHER PUBLICATIONS

Barash "Food and Drug Administration Memorandum concerning the Product: Tisseel" (FDA hereinafter), Pediatric Safety and Utilization Review for the Pediatric Advisory Committee (PAC) Meeting; Center for Biologies Evaluation and Research.*
Bullard KM, et al., Fetal Wound Healing: Current Biology. World J Surg 2003 : Jan. 27: pp. 54-61.
Chester, et al., A Review of Keratinocyte Delivery to the Wound Bed, The Journal of Burn Care & Rehabilitation, 2004; 25: pp. 266-275.
Clark, et al., Fibronectin and Fibrin Provide a Provisional Matrix for Epidermal Cell Migration During Wound Reepithelialization. Journal of Investigative Dermatology, 1982: vol. 79: pp. 264-269.
Ho et al., Greffes de Peau Artificielle dans le Traitement des Plaies Chroniques: Une Méta-Analyse de L'efficacité Clinique Et Une Étude Coûts-Efficacité. Rapport Technologique n° 52. Ottawa: Office Canadien de Coordination de L'évaluation des Technologies de La Santé 2005. pp. 1-71.
Hohlfeld, et al., Tissue Engineered Fetal Skin Constructs for Paediatric Burns, Lancet 2005: 366: pp. 840-842.
Hunyadi, et al., Keratinocyte Grafting: A New Means of Transplantation for Full-Thickness Wounds. Journal of Dermatologic Surgery and Oncology 1988: 14(1): pp. 75-78.
Jones, et al., Skin Grafting for Venous Leg Ulcers (review). The Cochrane library 2006: Issue I.
Rheinwald et al., Serial Cultivation of Strains of Human Epidermal Keratinocytes: The Formation of Keratinizing Colonies From Single Cells, Cell 1975: vol. 6: 331-344.
Shen, et al., Innovative Therapies in Wound Healing. Journal Cutaneous Medical Surgery 2003: pp. 217-224.
International Search Report and Written Opinion issued in corresponding International Application No. PCT/EP2013/076438, dated Mar. 5, 2014.
International Preliminary Report on Patentability issued in corresponding International Application No. PCT/EP2013/076438, dated Jun. 16, 2015.
Applegate, et al., "Whole-Cell Bioprocessing of Human Fetal Cells for Tissue Engineering of Skin," Skin Pharmacol Physiol 2009;22:63-73.
Hirt-Burri, et al. "Wound-healing Gene Family Expression Differences Between Fetal and Foreskin Cells Used for Bioengineered Skin Substitutes" 32(7)1509-518, Blackwell Publishing, Inc. 2008.

* cited by examiner

*Primary Examiner* — Louise W Humphrey
*Assistant Examiner* — Srikanth Patury
(74) *Attorney, Agent, or Firm* — Banner & Witcoff, Ltd.

(57) ABSTRACT

The present invention describes a composition comprising a mixture of human foetal keratinocyte cells and human foetal fibroblast cells, the ratio between said keratinocyte and fibroblast cells ranging from 0.75 to 2.5, preferably being 1:1 or 7:3. This composition is advantageously included in a bandage, said bandage preferably being sterile and packaged in a container impermeable to microorganisms. The present invention finally concerns the use of this composition as a drug, in particular for treating a skin defect (wound, burn or ulcer).

17 Claims, 13 Drawing Sheets

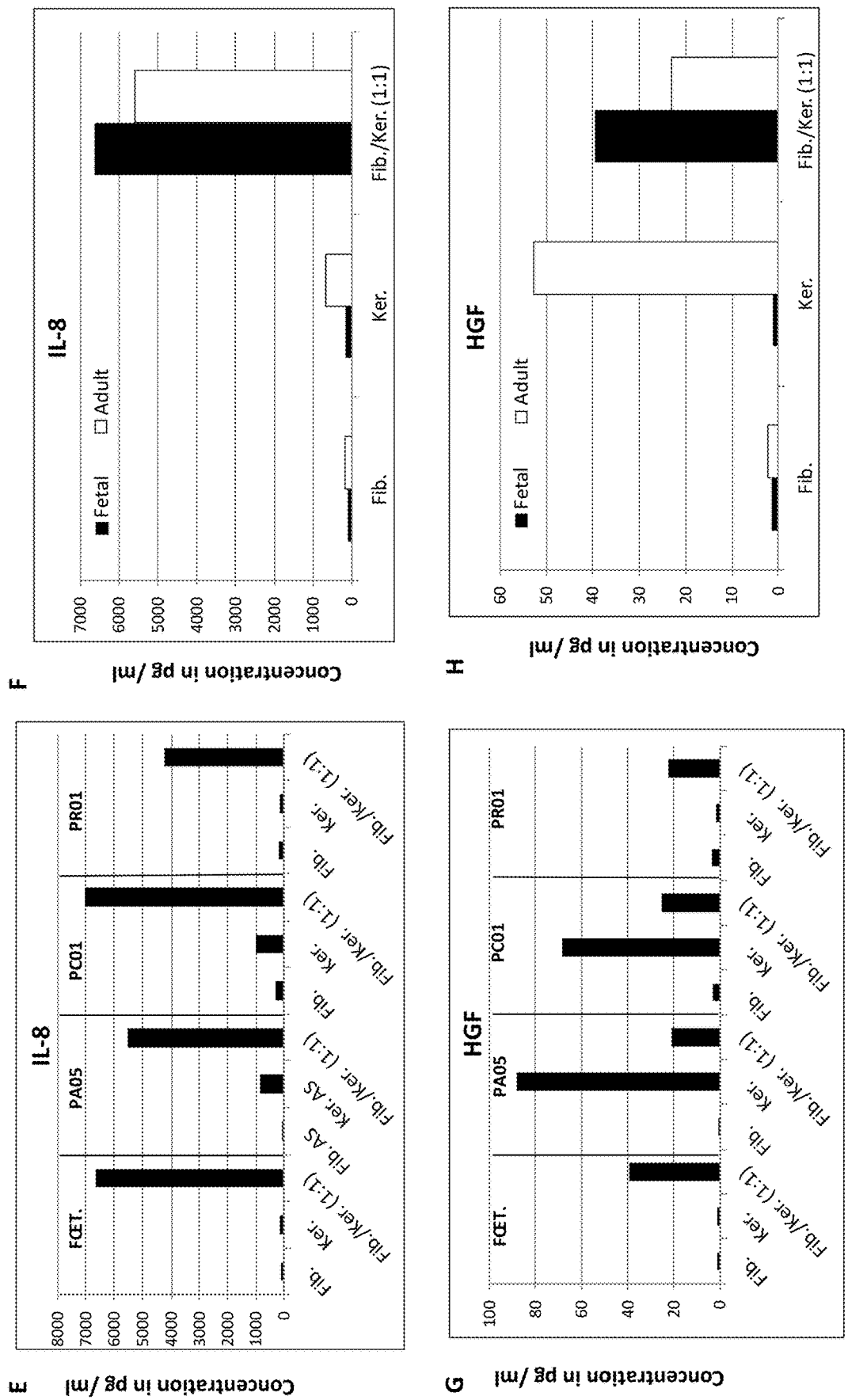
Figure 2 (continuation)

Figure 2 (continuation)
I
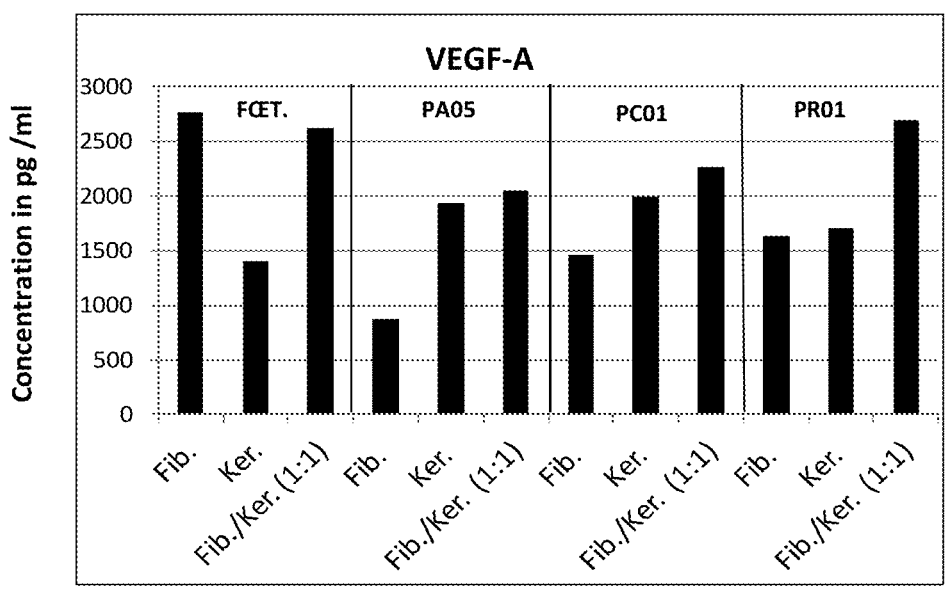
J
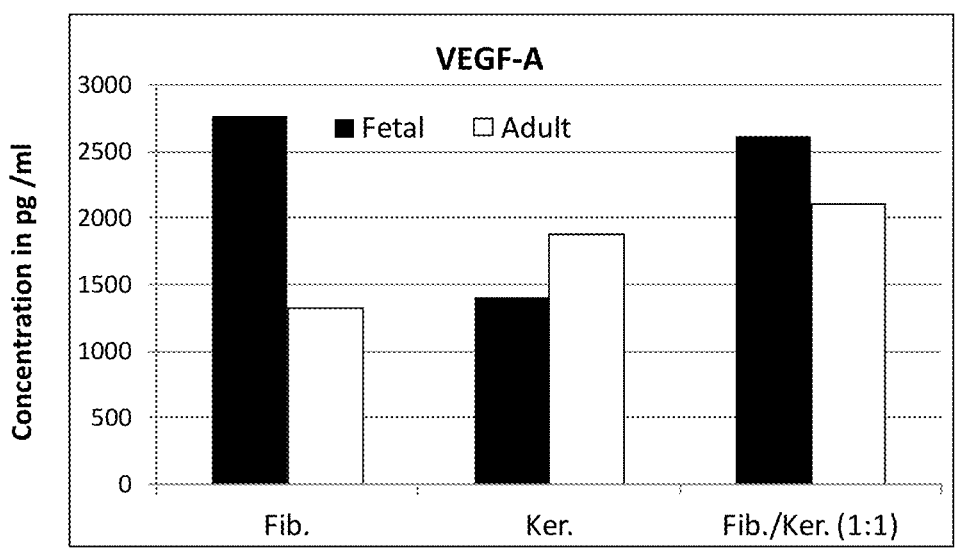

A

B

Figure 3 (continuation)
C
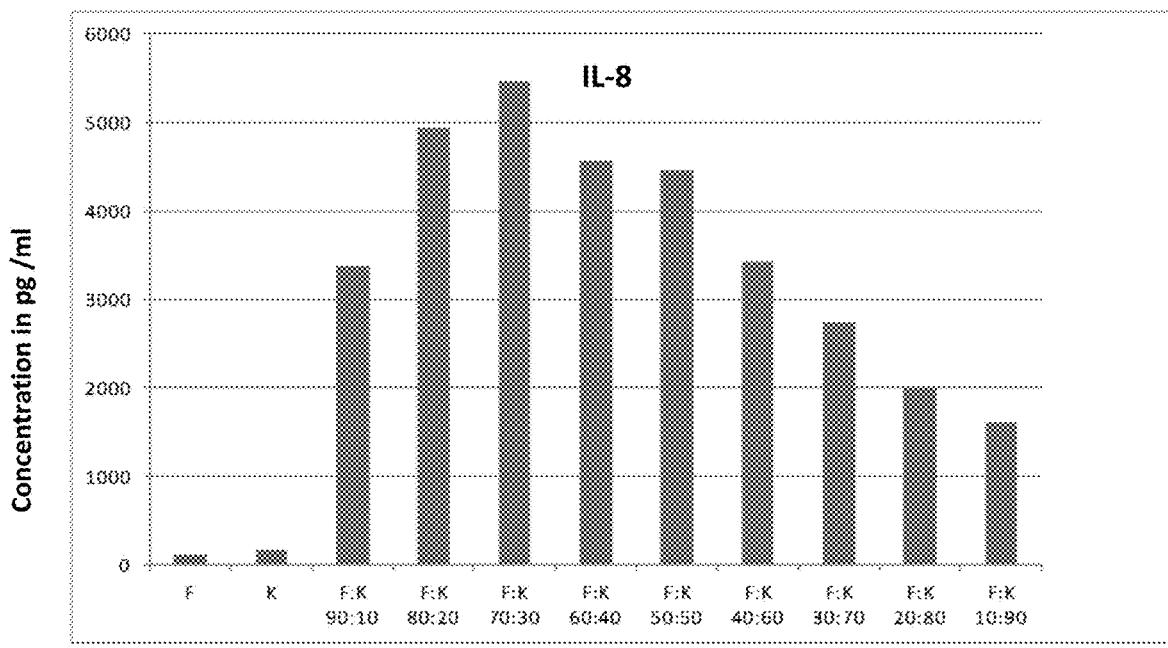
D
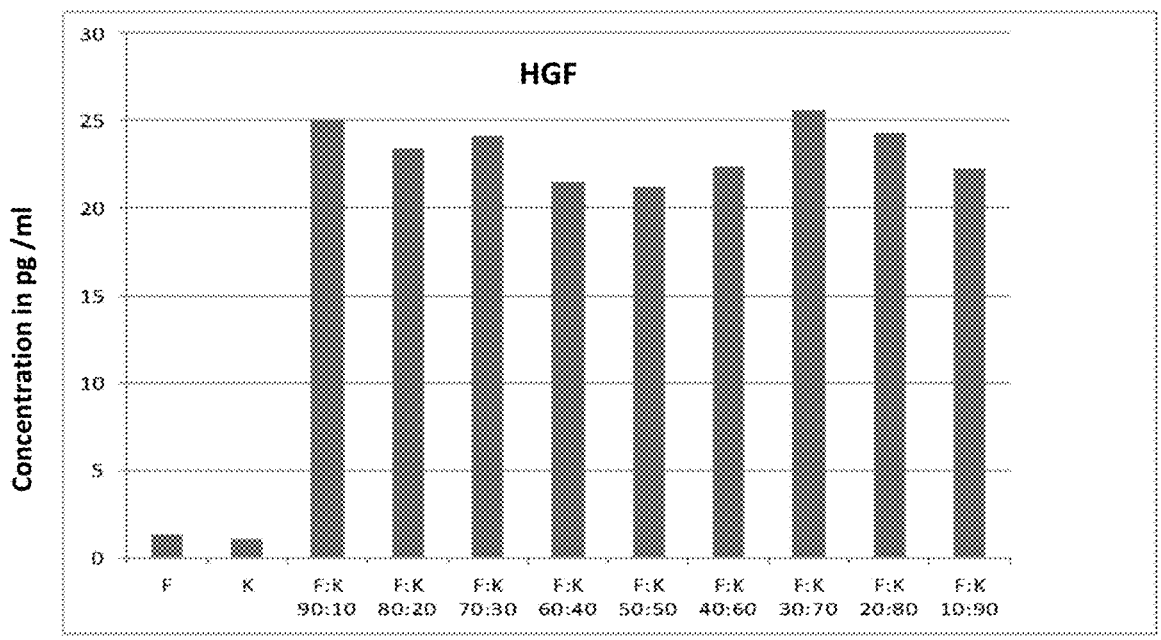

Figure 3 (continuation)
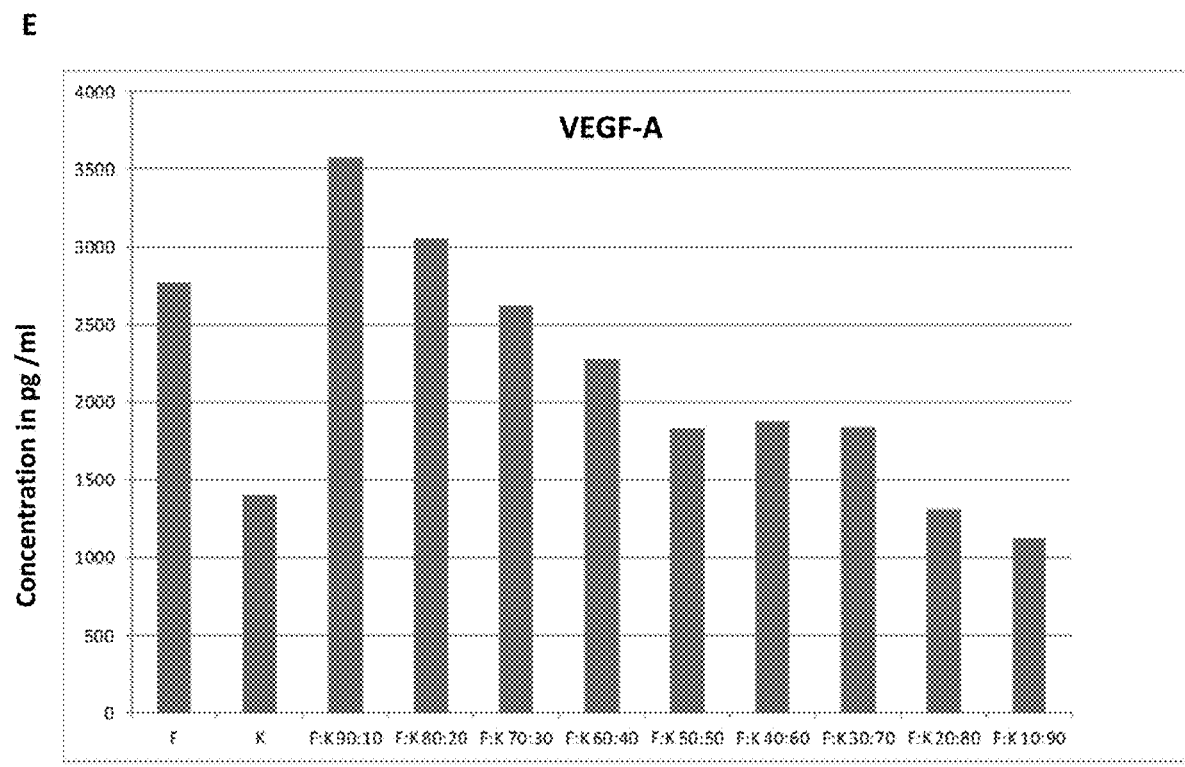

A

B

BANDAGE CONTAINING FOETAL FIBROBLASTS AND KERATINOCYTES

BACKGROUND OF THE INVENTION

Scarring of a wound is a natural and spontaneous phenomenon occurring without the intervention of a surgeon. Even though the fundamental processes of blood coagulation, fibrin deposit, synthesis and organisation of collagen have been studied for many years, the factors which trigger and control them are still not well understood. The evolution of wound healing can be modified by sophisticated endocrine, pharmacological and physical manipulations or, more simply, by surgical intervention, but the most important effects influencing healing of an open wound lies in the nature of the bandage which is applied to it.

To facilitate wound healing, it is possible to use a greasy bandage, a semi-occlusive bandage or an occlusive bandage (Begaud B. *Ann Dermatol Venereol* 2002). However, when the skin defect is large in size or remains refractory to conventional treatments, skin grafts are sometimes necessary to stimulate healing. These skin grafts can be taken from the patient himself in a non-lesional zone (autografts), but the autograft is sometimes still difficult since taking an autologous graft of an excessive size causes many healing problems at the level of the donor site, skin defects of venous ulcer type affect people already exhibiting healing disorders (elderly, diabetics).

In the event that the autograft is not possible, various artificial skin products can serve as substitutes to natural skin in the treatment of skin defects and allow normal skin to reform (Ho C, et al., Technological report No. 52. 2005). These substitutes can be classified into three categories: grafts of cultivated epidermis (which replace only the surface epidermis), dermal substitutes (which replace the lower dermal layer) and composite grafts (which consist in combining a dermal component and an epidermal component). Several products are available in each of these categories. Finally, a fourth category is represented by keratinocytes in suspension in a biological matrix. All previous clinical studies conducted with these different models of skin substitutes have shown no unwanted serious effect. All applications of these models have been tolerated by patients.

The epidermis grafts are generally obtained according to the technique of keratinocyte culture developed in 1975 by Rheinwald and Green (*Cell* 1975: 6: 331-344). This technique produces large quantity of epidermal platelets, by cultivating keratinocytes of a patient or donor on a layer of nourishing cells (irradiated murine fibroblasts). The confluent and differentiated platelets are transferred on a support prior to grafting. The keratinocytes placed into culture can be autologous (for Laserskin®, Epibase®) or allogenic (for CryoCeal). Using layers of allogenic keratinocytes produced from a donor other than the patient in fact reduces the wait period, but the risk of transmitting of viral diseases is considerable. The use of these culture epithelia has other disadvantages: first, the size of the platelets diminishes by 10 to 50% when they are enzymatically detached from the support which has served as their culture, and second, these platelets are fragile and difficult to handle (Chester D L, et al. *J Burn Care Rehabil* 2004; Shen J T and Falanga V. *J Cutan Med Surg* 2003). Also, the rate of grafting is also variable: the graft is often stable on a short term only and the neoderm renews only slowly. Finally, the absence of dermal constituents contributes to contraction of the wound, instability of the graft and formation of bubbles at the level of the graft.

To eliminate these problems, skin substitutes containing a dermal matrix (for example of Apligraf or Dermagraft brand) have been developed. These substitutes use allogenic cells only, contrary to epidermal substitutes.

More precisely, the Dermagraft is a living and active dermal structure from the metabolic viewpoint, containing allogenic fibroblasts of foreskin of neonates cultivated in a bio-resorbable trellis of polyglactin or glycolic acid (see U.S. Pat. No. 5,460,939). These fibroblasts favour synthesis of growth factors (PDGF, VEGF, . . . ), glycoproteins and proteins (collagen, fibronectin, . . . ) in situ, on the wound to be healed. This dermal matrix avoids problems of wound contraction and graft instability (Shen J T and Falanga V. *J Cutan Med Surg* 2003). Another dermal substitute is Apligraf® (or Graftskin®, see U.S. Pat. No. 4,837,379), which contains, in a type-I bovine collagen gel, allogenic foreskin fibroblasts from neonates. Allogenic keratinocytes which proliferate and differenciate are cultivated on this layer of fibroblasts. The cells constituting Apligraf® are capable of producing their own matrix and their own cytokines. This substitute does not contain antigen presenting cells such as Langerhans cells, or dendritic cells of the dermis, or endothelial cells or leucocytes. Yet, clinical trials aimed at demonstrating the clinical efficacy of Apligraf® or Dermagraft® for treatment of skin defects show insufficient evidence of the beneficial effect of these grafts (Jones J E and Nelson E A. The Cochrane library 2006). Also, the risk of transmitting viral illnesses is kept in check by using allogenic cells.

It is also possible to use autologous keratinocytes in suspension in a biological adhesive, such as the BioSeed®-S model, an autologous skin substitute containing adult autologous keratinocytes placed in suspension in a biological adhesive based on fibrin (Tissucol®) after 2 to 3 weeks of culture. The fibrin which stimulates the proliferation and migration of keratinocytes also ensures affixing of the cells onto the wound (Clark R A F et al. *J Invest Dermatol* 1982; Hunyadi J et al. *J Dermatol Surg Oncol* 1988). After grafting, keratinocytes pre-confluent in suspension can form a better developed and more resistant continuous basal membrane with a dermo-epidermal junction, as demonstrated in a porcine model (Chester D L. et al. *J Burn Care Rehabil* 2004). However, such autologous systems are available only after amplification of the patient cells and therefore require several weeks before they can be used. This very long delay is prohibitive in some urgent situations (post-surgical skin covering or burns).

Besides to date, there is no proof that any one of available bandages containing cells of neonates or adults (autologous or not) effectively accelerates wound healing.

The use of foetal cells for treating of skin defects has many advantages compared to adult cells. In fact, skin repair in a foetus of under 24 weeks' gestation is followed by rapid healing without scarring, in contrast to adult skin (Bullard K M et al. *World J Surg* 2003; Hohlfeld J, et al. *Lancet* 2005). This phenomenon seems to be inherent to foetal skin of under 24 weeks and is independent of the intra-uterine environment. These properties, unique to foetal cells, are due to the profile of secreted cytokines and the gene expression of these cells (Bullard K M et al. *World J Surg* 2003). The inflammatory infiltrate is also less important and tolerance of foetal cells is better.

There is currently just a single model of skin substitute based on foetal skin cells (Neocutis®). This skin substitute contains a fixed quantity of foetal human cells coming from a single cellular bank, constituted by a mixture of 90% of fibroblasts and 10% of keratinocytes. The present inventors have noted in an in-vitro healing model that a ratio between keratinocyte and foetal fibroblast cells ranging from 0.75 to 2.5, preferably from 1:1 (50% keratinocytes and 50% fibroblasts), or even from 7:3 (70% keratinocytes and 30% fibroblasts), seemed optimal for healing.

In this context, the present inventors have researched a system which, i) by control of the foetal keratinocytes/fibroblast ratio allows the optimisation of healing especially by controlling the quantity and nature of growth factors and secreted cytokines ii) by the nature of the foetal cells guarantees good immunotolerance and a decrease in local inflammation.

Thanks to two separate cellular banks constituted specifically by keratinocytes or foetal human fibroblasts, the inventors have demonstrated by an in-vitro test that use of these cells in a ratio of about 1:1, or about 7:3, would produce optimal healing. These ratios have therefore been selected for treatment of wounds and skin defects. The application of foetal cells in such proportions stimulates keratinocytes and fibroblast cells of the recipient thanks to the secretion (by foetal cells) of specific cytokinin factors. In addition, the foetal origin of cells of the system, by the production of specific cytokines, substantially limits the risk of rejection.

FIGURES

FIG. 1 illustrates the production of VEGF A factors (top graphic), PDGF-AA (middle graphic) and of IL-1β (lower graphic) in the supernatant of keratinocytes and foetal fibroblast cells obtained from donor BKF 07, and in the supernatant of the mixture at the ratio 1:1 of fibroblast cells and keratinocytes from the same donor.

FIG. 2 illustrates the production of factors GM-CSF (FIGS. 2A and 2B), IL-1a (FIGS. 2C and 2D), IL-8 (FIGS. 2E and 2F), HGF (FIGS. 2G and 2H), and VEGF-A (FIGS. 2I and 2J) in the supernatant of keratinocytes and foetal fibroblast cells obtained from donor BKF 07, alone or mixed at a ratio 1:1, as well as in the supernatant of keratinocytes supernatant and adult fibroblast cells, alone or mixed at a ratio 1:1 (PA: cells coming from an abdominoplasty of an adult donor; PC: cells coming from thigh surgery of an adult donor; PR 01: cells coming from the foreskin of an adult donor). For each cytokine, two types of graphics are presented. Graphics A, C, E, G and I illustrate the results of dosages of cytokines for each sample of donor tested, while graphics B, D, F, H and J illustrate comparison of the production of cytokines of the average of samples of adult cells to that of cells of foetal origin.

FIG. 3 illustrates the production of GM-CSF (FIG. 3A), IL-1α (FIG. 3B), IL-8 (FIG. 3C), HGF (FIG. 3D), and VEGF-A (FIG. 3E) in the supernatant of keratinocyte cells (K) and foetal fibroblast (F), alone or mixed at different ratios.

FIG. 4 illustrates the characterisation of foetal keratinocytes and fibroblast cells obtained from donor BKF 07. FIG. 4A, Phase contrast microscopy photography of cells in confluent culture coming from clinical batches of keratinocytes (left image) and fibroblasts (right image). FIG. 4B, Histogram of cytometry indicating the percentage of cells expressing keratin 14 within the clinical batch of keratinocytes (left histogram) and the percentage of cells expressing prolyl-4-hydroxylase within the clinical batch of fibroblasts (right image). FIG. 4C, Fluorescence microscopy photography indicating the expression of keratin 14 and prolyl-4-hydroxylase on cellular mats obtained after thawing cells of the clinical batch of keratinocytes (left image) and of the clinical batch of fibroblasts (right image). FIG. 4D, Cytograms showing the expression of integrins ß1, α2 and α3 by keratinocytes (left cytogram) and foetal fibroblasts (right cytogram). They show that keratinocytes strongly express integrins ß1, α2 and α3, whereas the fibroblasts express integrin 131 only.

FIG. 5 illustrates inhibition of the proliferation of peripheral blood monocyte cells (PBMC) by the foetal fibroblast cells only (ratio of fibroblast cells/PBMC: 1/4, 1/20, 1/100 and 1/200), by the foetal keratinocyte cells only (ratio of keratinocyte cells/PBMC: 1/4, 1/20, 1/100 and 1/200), or by the mixture of keratinocytes and fibroblasts 1:1 (ratio of fibroblast cells and keratinocyte/PBMC: 1/4, 1/20, 1/100 and 1/200). For different conditions, the results are expressed in a percentage of the proliferation relative to the positive control (PBMC stimulated with PHA-L and IL-2 without foetal cells). (FIG. 5B) illustrates inhibition of lymphocyte proliferation by the foetal fibroblast cells only (ratio of fibroblast cells/PBMC: 1/4)(a), by the keratinocyte cells only (ratio of keratinocyte cells/PBMC: 1/4)(b), or by the mixture of keratinocytes and fibroblasts 1:1 (ratio of fibroblast cells and keratinocyte/PBMC: 1/4)(c) in the presence or not of the specific inhibitor of IDO (indoleamine 2,3 dioxygenase) the 1-MT (1-methyl tryptophane) used in concentrations of 200 µM, 20 µM and 2 µM.

DETAILED DESCRIPTION OF THE INVENTION

Figure 1:
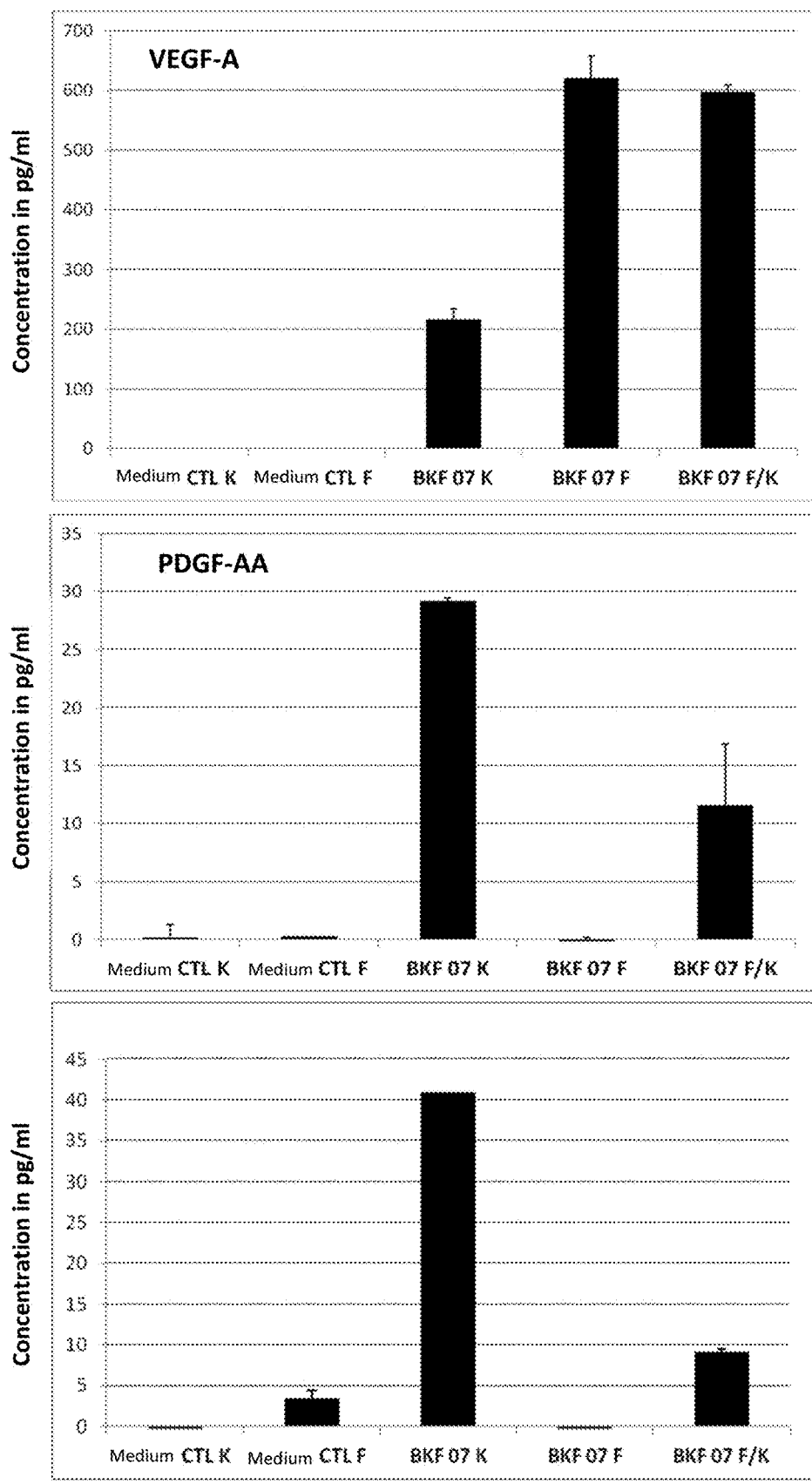

For the first time, the inventors have built two banks of separate foetal human cells, one containing foetal human keratinocyte cells, the other containing foetal human fibroblastic cells. Setting up these two banks has allowed them to study the influence of each of these cellular types on skin wound healing. It thus allowed them to develop a composition in which the proportion of fibroblasts and/or foetal human keratinocytes is precisely adapted to effectively stimulate skin healing, notably via the secretion of growth factors produced by fibroblasts and foetal keratinocytes.

The originality of this composition lies in the particular proportion of fibroblasts and/or foetal human keratinocytes identified by the inventors, which has never been proposed to this day. This particular proportion accelerates the healing process.

The advantages of such a composition are numerous:

On one hand, from a purely practical viewpoint, this composition does not require differentiated epidermis or dermo-epidermal junction, and it can be made available to a patient within 48 to 72 hours following request. Besides, each component (keratinocytes or fibroblasts) of the composition can be easily transported over distance, preferably in frozen ampoules in a container in nitrogen vapour.

On the other hand, the foetal origin of cells which are present provides to this composition a perfect tolerance and a minimal risk of rejection.

Finally, from a theracanic viewpoint, foetal cells present in this composition secrete a large number of cytokine factors (for example PDGF-AA, VEGF-A, GM-CSF, HGF) which play an essential role in healing by efficaciously stimulating angiogenesis, migration and cellular proliferation, presaging rapid and high-quality healing.

The present invention therefore relates, in a first aspect, to a composition comprising a mixture of foetal human keratinocyte cells and foetal human fibroblastic cells, the ratio between said keratinocyte and fibroblast cells ranging from 0.75 to 2.5. According to a preferred embodiment of the invention, said ratio is comprised between 0.75 and 1.25, and more preferably is 1:1. According to another preferred embodiment, said ratio ranges from 1.25 to 2.5, and more preferably is 7:3.

According to the present invention, the term "composition" designates a mixture of foetal human keratinocyte cells and foetal human fibroblast cells, suspended in or integrated into a non-immunogenic medium adapted to their survival and their migration (for example collagen, fibrin, chitosan), said medium favouring (or in any case not preventing) secretion of cytokines and growth factors naturally secreted by said cells, especially "Vascular Endothelial Growth Factor" (VEGF), "Platelet-Derived Growth Factor" PDGF-AA, and interleukin 1-beta (IL1β). Said medium also favours (or in any case does not prevent) the immunomodulator capacity exerted by said cells. In particular, this composition can be considered as a skin substitute, since, when applied to a wound, a lesion, a burn, or a skin defect in an animal or human subject, it favours regeneration of the damaged skin by i) migrating rapidly towards the lesion to reconstitute the dermis and/or epidermis, ii) positively influencing the migration of cells of the subject via the growth factors they secrete and iii) limiting local inflammation due to its immunosuppressive properties.

According to the present invention, "foetal human keratinocyte cells" means keratinocyte cells of foetal origin, i.e., obtained from foetal human skin, said cells having the following specific features: i) typical morphology of epithelial cells, ii) a propensity for secreting essential growth factors and cytokines in the healing process, iii) tolerogenic properties and iv) strong migration capacity. Advantageously, the foetal human keratinocyte cells used in the composition of the invention secrete cytokines and specific growth factors of keratinocytes (for example PDFG-AA and IL-1β), express one or more known markers of keratinocytes precursors (for example keratin 14, keratin 5, or keratin 15), and exhibit functional migratory properties (for instance, expression of integrins β1, α2 and α3) and immunosuppression linked to their foetal origin and based on Indoleamine-2,3-dioxygenase (IDO) enzymatic activity (cf. FIG. 5B b). These specific features can be shown by any technique conventionally used for this effect, and notably by conventional microscopy, Elisa dosage, flow cytometry (FACS), immunofluorescence, and lymphocyte proliferation test.

These foetal keratinocyte cells can be obtained by any process known to those skilled in the art for conserving the above properties. In particular, they can be obtained by placing explants of foetal human skin into culture to enable keratinocytes to exit from the explants then proliferate in an appropriate medium. Such media are widely described in the literature. It is possible to use for example medium CnT-07 as sold by CELLnTEC, medium KGM2 as sold by Promocell, medium KSFM as sold by Invitrogen, optionally supplemented by classic antibiotics to avoid contamination by bacteria during the cellular culture step.

To generate foetal human keratinocyte cells usable in the composition of the invention, the inventors advantageously use a particular protocol to separately obtain, from the same sample of foetal human skin, keratinocyte cells and foetal human fibroblastic cells (cf. example I, section 1.3). This protocol is described in example I+III herein below. To summarise briefly, the sample of foetal skin was rinsed by immersion in a buffered saline culture medium (for example, "phosphate buffered saline" (PBS) medium or "Dulbecco's phosphate buffered saline" (DPBS) medium), then cut out in explants of small size (around 1 mm per side) which were placed in culture plaques, then were covered in a classic culture medium (for example MEM or DMEM complemented by 20% foetal calf serum and 1% penicillin-streptomycin) before being incubated at 37° C. in humid atmosphere with 5% $CO_2$ over an average 10 to 15 days. A change in medium was made by taking off half of the medium and adding the equivalent of fresh medium after 5 days of culture. According to this process particular, the fibroblasts are unstuck by enzymatic action (trypsin EDTA) over a short period of 5 to 10 minutes so that only the fibroblasts detach while the keratinocytes remain adherent. The fibroblasts in suspension are transferred to a tube, centrifuged and returned to culture in a culture flask. The wells containing no more than keratinocytes remaining adherent are rinsed with a medium which inhibits trypsin action (for example DMEM, SVF 10%). After rinsing wells with DPBS, keratinocyte growth is favoured by replacing the initial culture medium by a culture medium appropriate to keratinocytes proliferation (for example CnT-07 medium) supplemented by antibiotics. After 5 to 7 days of culture at 37° C. in humid atmosphere with 5% $CO_2$ after elimination of fibroblasts, the keratinocyte cells are detached by trypsin action then seeded in a culture flask. The cells are incubated 5 to 7 additional days then detached by trypsin action and finally frozen at P1 to constitute an initial bank of keratinocyte cells. In a particular embodiment of the invention, an aliquot of this initial bank is thawed, the keratinocyte cells are amplified at 37° C. in humid atmosphere with 5% $CO_2$ as far as the third pass, P3 (a fortnight of culture after thawing of cells coming from P1), then frozen to constitute a clinical batch (or "bank of cells") of foetal keratinocyte cells of interest usable in the composition of the invention.

These foetal keratinocyte cells can be frozen by any process known to those skilled in the art using for example a solution of freezing compound of a proteic solution (for example Human Albumin 40 mg/mL) combined with cryoformulator (for example Dymethyl Sulfoxide) at a 9:1 ratio.

Once this clinical batch is formed, the foetal human keratinocyte cells integrated into the composition of the invention no longer need to be extemporaneously generated from foetal skin since they can be directly obtained from the clinical batch of foetal human keratinocyte cells, by reculturing a sample of foetal human keratinocyte cells in an appropriate medium (for example the above CnT-07 medium).

According to the present invention, "foetal human fibroblastic cells" means fibroblast cells of foetal origin, i.e., obtained from foetal human skin, said cells having the following specific features: i) typical morphology of fibroblast cells, ii) propensity to secrete growth factors and cytokines essential in the healing process, iii) tolerogenic properties and iv) strong migration capacity. Advantageously, the foetal human fibroblastic cells used in the composition of the invention strongly secrete cytokines and growth factors such as VEGF-A, and express one or more known markers of fibroblasts such as prolyl-4-hydroxylase.

Figure 5A:
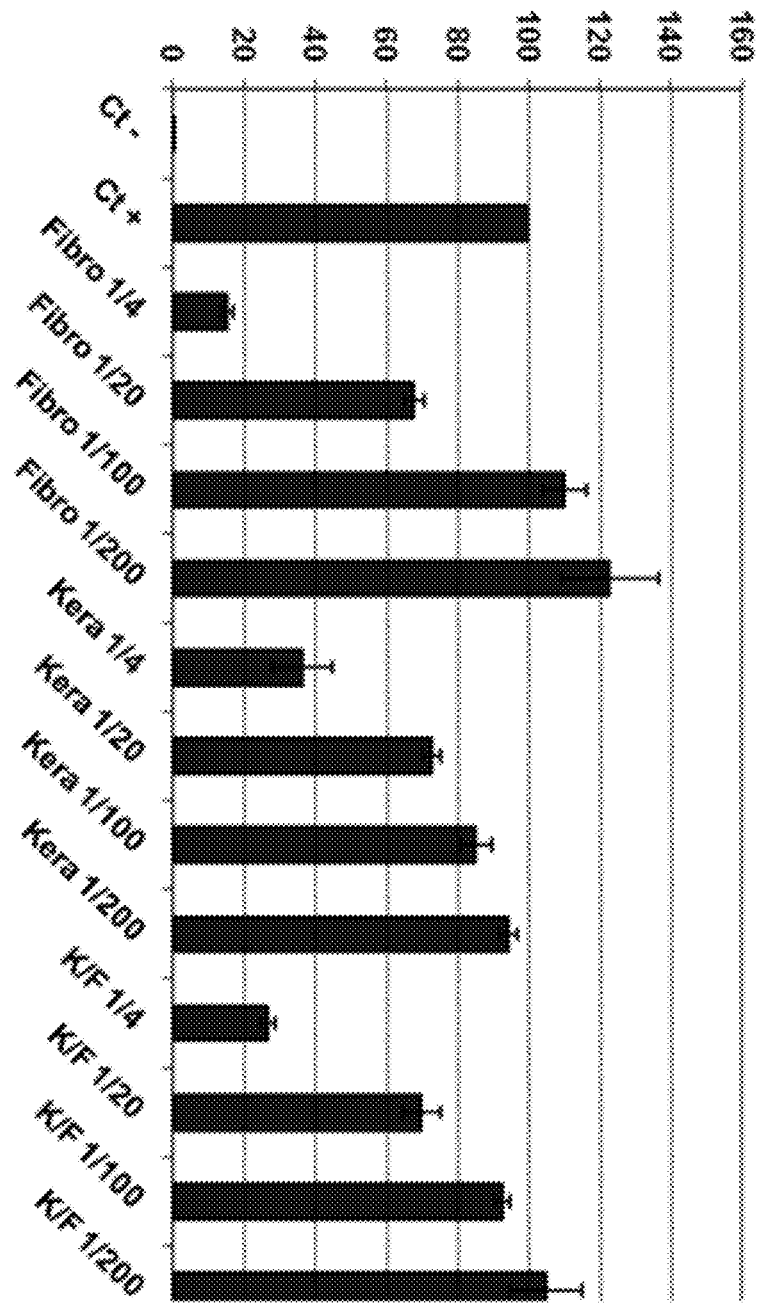
Figure 5B:
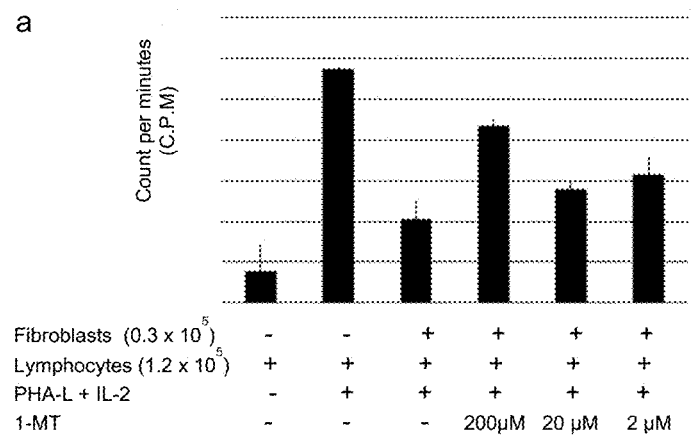
Figure 5B:
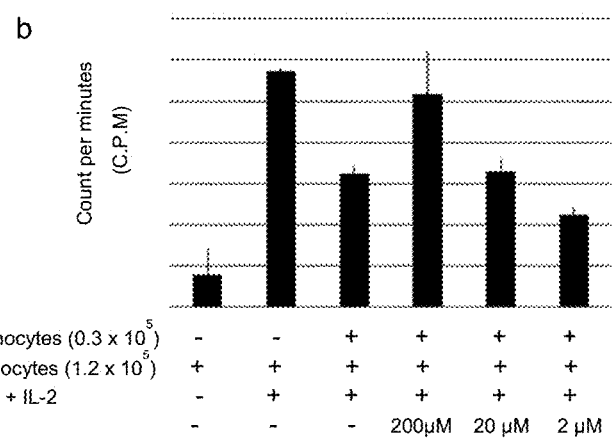
Figure 5B:
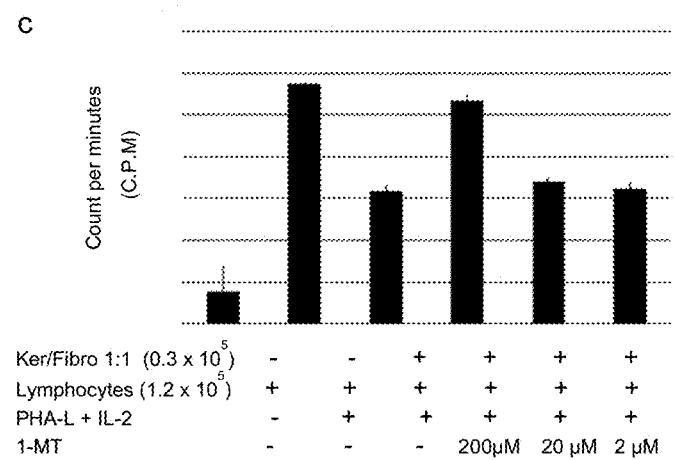

They exhibit functional migratory properties (for example expression of integrin β1), and immunosuppression linked to their foetal origin and based on the enzymatic activity of Indoleamine 2,3 dioxygenase (IDO) (cf. FIG. 5B a). These specific features can be revealed by any technique conventionally used for this effect, and notably by conventional microscopy, Elisa dosage, flow cytometry (FACS), immunofluorescence, and lymphocyte proliferation test.

These foetal fibroblast cells can be obtained by any process known to those skilled in the art for preserving the above properties. They can be notably obtained by placing explants of foetal human skin in culture, enabling fibroblast cells to exit from explants, then their proliferation in an appropriate medium. Such media are widely described in the literature. It is possible to use for example, MEM or DMEM supplemented by 20% SVF and conventional antibiotics to avoid contamination by bacteria during the cellular culture step.

It is also possible to use the particular protocol described in example I (section 1.2) mentioned herein below. According to this protocol, which allows the obtention of both fibroblasts and keratinocytes from the same sample of foetal skin, the foetal fibroblast cells are obtained by rinsing said sample of foetal human skin in a buffered saline culture medium (for example medium PBS or DPBS), then by placing skin explants on culture plates which are then covered by a classic culture medium (for example DMEM complemented by 20% foetal calf serum and 1% penicillin-streptomycin) before being incubated at 37° C. in humid atmosphere with 5% $CO_2$ for an average of 10 to 15 days. A change of medium is made by taking off half of the medium and adding the equivalent of fresh medium after 5 days of culture. According to this particular process, the fibroblasts are unstuck by enzymatic action (trypsin EDTA) over a short time, from 5 to 10 minutes, such that only the fibroblasts detach whereas the keratinocytes remain adherent. The fibroblasts in suspension are transferred to a tube, centrifuged and returned to culture at 37° C./5% $CO_2$ in a flask in a classic medium, such as DMEM supplemented by 10% SVF.

A change of medium is made by taking off half of the medium and adding the equivalent in fresh medium every 3 to 4 days. After 10 to 15 days of culture, the cells are detached by action of trypsin-DETA then frozen at P1 to constitute an initial bank of fibroblast cells. In a particular embodiment of the invention, a sample of this initial bank is thawed, the fibroblast cells are amplified at 37° C. in humid atmosphere with 5% $CO_2$ to the third pass (P3, twenty days of culture after thawing of cells coming from P1), then frozen to constitute a clinical batch of foetal fibroblast cells of interest usable in the composition of the invention.

These foetal fibroblast cells can be frozen by any process known to those skilled in the art, for example using a freezing solution comprising a protein solution (for example Human Albumin 40 mg/mL) associated with a cryoformulator (for example Dymethyl Sulfoxide) at a 9:1 ratio.

Once the clinical batch is constituted, the foetal human fibroblast cells integrated into the composition of the invention no longer need to be extemporaneously generated from foetal skin because they can be directly obtained from the clinical batch of foetal human fibroblast cells constituted by reculturing a sample of foetal human fibroblast cells in an appropriate medium (for example the abovementioned DMEM medium).

Preferably, skin used to produce the keratinocyte and fibroblast cells used in the composition of the invention is sampled from a human foetus aged 18 to 24 weeks, even more preferably from a human foetus aged 18 to 20 weeks.

The human keratinocyte and foetal fibroblast cells must be present in the composition of the invention according to very precise proportions to induce efficacious and rapid healing of the skin lesion. Thus, the ratio between the number of keratinocyte cells and the number of fibroblast cells (keratinocytes/fibroblasts) in the composition of the invention can range from 0.75 to 2.5. In a preferred embodiment, the ratio between the number of keratinocyte cells and the number of fibroblast cells (keratinocytes/fibroblasts) is comprised between 0.75 and 1.25, preferably between 0.85 and 1.15, and most preferably is 1:1. In an alternative preferred embodiment, the ratio between the number of keratinocyte cells and the number of fibroblast cells (keratinocytes/fibroblasts) ranges from 1.25 to 2.5, preferably from 1.5 to 2.5, from 1.75 to 2.5, from 2 to 2.5, from 2.25 to 2.5, and most preferably is 7:3.

Techniques for counting cells are very well described today and are reliable to a few percent (typically, from 2 to 5%). It is possible to use for example automatic cell counters (especially the "Cellcounter®" system sold by Millipore, Invitrogen or Biorad) or to manually count cells by using dedicated numbering cells (Malassez cells, from Thoma). It is important to use the same counting system to determine the quantity of each cellular type so that any error due to numbering technique is the same.

In a particular embodiment, apart from keratinocytes and foetal human fibroblast cells, the composition of the invention contains a natural or synthetic, non-immunogenic extracellular matrix, preferably for humans. More precisely, the human keratinocyte and foetal fibroblast cells of the composition of the invention are integrated into an extracellular matrix constituted by collagen of type I of bovine origin. It should be noted that bovine collagen has been accepted by French regulatory agencies for clinical use in humans. In fact, this type of xenogenic matrix does not induces an immunitary response in the patient due to the low immunogenicity of collagen.

The term "extracellular matrix" here designates a set of extracellular macromolecules naturally present in connecting tissue and other tissues of multicellular organisms. This matrix is largely made of glycoproteins and pure proteins, as well as glycosaminoglycanes, which forms a matricial network. It plays a role in structural support, adherence, movement and regulation of cells within tissue. Proteins of the natural extracellular matrix are more precisely collagen, elastin, fibronectin, laminin, proteoglycanes, vitronectin, thrombospondin, tenascin (cytoactin), entactin (nidogen), osteonectin (SPARC), anchorin CII, chondronectin, epinectin, hyaluonectin, the compound P amyloid, fibrillin, merosin, laminin S, undulin, epilligrin and kalinin.

By "Non-immunogenic" matrix, it is meant herein that this matrix is made of compounds which do not induce (or very little) immunitary response in individuals for whom the composition is intended. Preferably, said matrix is non-immunogenic for humans. An "allogenic" matrix for humans means that it is essentially made of proteins or compounds of human origin. A "xenogenic" matrix for humans is per se essentially made of proteins or compounds of animal origin (other than human). The two types of matrix can be used in the composition of the invention. But, in the event where a xenogenic matrix is used, it should be ensured that the latter is minimally immunogenic for humans (such as bovine collagen for example).

Polymeric compounds produced artificially (otherwise called "hydrogels") can also be used. Those skilled in the art can identify and select which compound (artificial or natural) is adapted as a function of the preferred therapeutic application.

In a preferred embodiment, the keratinocytes and foetal human fibroblast cells of the composition of the invention are integrated in an extracellular matrix containing at least one compound natural selected from: collagen, fibrin, laminin, fibronectin, elastin, chitosan, and heparin. In a yet more preferred embodiment, the keratinocytes and foetal human fibroblast cells of the composition of the invention are integrated in an extracellular matrix containing at least one compound selected from: collagen, fibrin, fibronectin, and elastin. In the most preferred embodiment, the keratinocytes and foetal human fibroblast cells of the composition of the invention are integrated in an extracellular matrix containing at least one compound selected from: human collagen, human fibrin, human fibronectin, and human elastin. It is also possible to integrate the keratinocytes and foetal human fibroblast cells in an extracellular matrix containing at least one compound selected from: bovine collagen, bovine fibrin, bovine fibronectin, and bovine elastin.

Advantageously, the intralesional adhesive called "Tissucol®" from Baxter laboratories can be used as extracellular matrix in the composition of the invention. This adhesive contains human fibrinogen, human factor XIII, human fibronectin, plasminogen, bovine aprotinin and human thrombin. More precisely, this adhesive contains, for 0.5 mL of reconstituted solution, 45 mg of human fibrinogen, 5 UI of human coagulation factor XIII (one unit of factor XIII corresponding to the activity contained in 1 mL of fresh plasma), 2.75 mg of human fibronectin, 0.04 mg of human plasminogen, 0.83 UPE (European pharmacopoeia unit) of bovine aprotinin and 250 UI of human thrombin. This intralesional adhesive is endowed with properties of hemostasis, collage, adhesion and tightness of tissues and also favors healing of surgical wounds. It can be used in patients undergoing anti-coagulant treatment or having hemostasis defects. The mode of action of this adhesive reproduces the final phase of coagulation: fibrinogen transforms into insoluble fibrin under the action of calcic thrombin and factor XIII. The resulting fibrin physically and chemically adheres to the treated tissues and exhibits a high degree of reticulation. Thrombin, fibrin and factor XIII have an effect favoring the proliferation of fibroblasts. The following step of the wound-healing process consists in proteolytic and phagocyte degradation of the fibrin network. Fibrinolysis depends also on the activators of the tissular plasminogen, of which the concentration can vary depending on organs and tissues. Aprotinin added to the fibrin adhesive inhibits the fibrinolysis induced by plasmatic and tissular proteases over a fortnight, according to location. The final step is the substitution of the fibrin layer by cicatricial connective tissue. This adhesive can be reconstituted according to the instructions of the manufacturer.

It is finally possible to use, as extracellular matrix in the composition of the invention, human or bovine collagen which is the principal constituent of the extracellular matrix in the dermis and is therefore the natural support of fibroblasts and keratinocytes. Type-I collagen will preferably be used here, which constitutes the weft of the connective tissues, and which is the predominant matricial element of the dermal tissue.

It is said that keratinocytes and foetal human fibroblast cells are "integrated" in the extracellular matrix when inserted in the matricial network created by the entangling of the compounds of this matrix. In practice, a composition is obtained in which cells are integrated by mixing the cells with the constituent(s) of the matrix. The protocol varies depending on the matrix used. For example, when the adhesive "Tissucol" is used, the fibroblast cells and foetal human keratinocytes can be directly mixed with thrombin and factor XIII, then fibrinogen can be added, and the whole can be directly applied to a skin defect such as a wound, a burn or an ulcer and form a solid gel.

In another embodiment, the composition of the invention can be obtained by adding the culture medium containing keratinocytes and foetal human fibroblast cells to the already constituted matrix and waiting until the cells penetrate therein by migration. Once the cells have started to be distributed through the extracellular matrix, the culture medium adapted to their growth will allow colonisation of the entire matrix by the cells.

In a second aspect, the invention therefore more generally relates to a process for manufacturing a composition, comprising the step of mixing foetal human keratinocyte cells and foetal human fibroblastic cells with a non-immunogenic extracellular matrix, in a ratio ranging from 0.75 to 2.5. The preferred ranges and values of said ratio described herein above apply mutatis mutandis to the present aspect of the invention.

In a particular embodiment, this process comprises, prior to the mixing step, the two steps of:
 a) obtaining foetal human keratinocyte cells, and
 b) obtaining foetal human fibroblastic cells.
These cells have been described herein above.

Preferably, the process of the invention does not comprise a step of placing said cells into culture between the step(s) for obtaining the latter and the step of mixing the cells with the extracellular matrix. In this way, after they are produced, the keratinocyte cells and foetal human fibroblasts can be directly mixed with the extracellular matrix. This particular preparation mode allows to increase in the cells viability of the composition according to the invention. According to this particular embodiment, said extracellular matrix is preferably a matrix of collagen such as type-I collagen.

Preferably, these keratinocytes and foetal human fibroblast cells are obtained from two separate banks containing these cells. In this case, the manufacturing process of the invention comprises the two steps of:
 a) obtaining a bank of foetal human keratinocyte cells, and
 b) obtaining a bank of foetal human fibroblastic cells.

By way of routine handling, the skilled person in the art knows how to easily determine the adequate concentration and/or density of the keratinocytes and foetal human fibroblast cells in the extracellular matrix depending on the preferred application (in fact, some wounds or burns can require a concentration of cells more or less high depending on their degree).

Similarly, by way of simple routine tests, those skilled in the art know exactly how to set the quantity and/or concentration of each constituent of the extracellular matrix to obtain the preferred degree of reticulation (influencing the spacing of fibers in the matricial network, which must not impair migration of keratinocytes and foetal human fibroblast cells). The inventors have identified that when the composition contains an extracellular matrix, it is recommended to introduce between $0.1 \times 10^6$ and $5 \times 10^6$ cells per $mL/cm^3$ of matrix.

To attain the ideal quantity of keratinocytes and foetal human fibroblast cells in the composition of the invention, it is possible to directly introduce the total preferred number of cells, or even introduce a lower number then place the composition in culture in an adapted medium (for example DMEM complemented by SVF at 10%) for several days to let the keratinocytes and foetal human fibroblast cells migrate and proliferate in the matrix to obtain an optimised bandage prior to application to the wound.

Application of the composition of the invention to damaged skin (wounded or burnt) can be done by any means known in the art not affecting the viability and mobility of cells it contains. For example, the composition of the invention can be applied on the wound using a syringe or by way of a bandage which holds the localised composition on the wound. Depending on its method of administration, the composition of the invention can also contain a pharmaceutically acceptable excipient such as an antibacterial agent, an anti-fungal agent, or any solvent conventionally used in compositions that can be administered topically. Those skilled in the art can determine exactly which excipients can be used in the composition of the invention, to the extent where they do not affect the secretion of growth factors and cytokines or the mobility and proliferation of cells present in the composition.

The composition of the invention is preferably used on humans. It can nevertheless be used in veterinary applications, notably on domestic animals such as dogs, cats, horses, etc.

In a third aspect, the present invention also relates to the composition of the invention for use for treating any skin defect, such as for example a wound, a burn or an ulcer and/or regenerating the skin and/or accelerating the healing of any skin defect, for example a wound, a burn or an ulcer. The invention also focuses on the use of the composition of the invention for manufacturing a bandage or a drug intended for regenerating skin, accelerating healing or tending to any skin defect, for example a wound, a burn, an ulcer. The invention finally relates to a method for regenerating skin, and/or tending to and/or accelerating healing of any skin defect, for example a wound, a burn or an ulcer comprising the local application of the composition of the invention to said skin defect.

In a fourth aspect, the invention finally relates to a bandage containing the composition of the invention such as defined herein above. By "bandage", it is meant herein a protective device for covering a damaged part of the skin.

In a preferred embodiment, the bandage of the invention is sterile and packaged in a container impermeable to microorganisms. In this bandage, the composition of the invention is covered for example by a plasticizer which can be selected from the group consisting of: glycerol, propylene glycol, polyethylene glycol, polypropylene glycol, sorbitol, other glycols and ether glycols such as mono- or diethers of polyalkylene glycol, mono- or diesters of polyalkylene glycol, glycolates of polyethylene glycol, ethylene glycol, diethylene glycol, triethylene glycol, dipelargonate of propylene glycol and glycerol of polypropylene glycol, sorbitan esters, esters of citric and tartaric acid, amphoteric surface agents derived from imidazoline, lactames, amides, polyamides, compounds of quaternary ammonium, esters such as phthalates, adipates, stereates, palmitates, sebacates or myristates and combinations thereof, diisopropyl adipate, phthalates and diethyl sebacate; hydrocarbides such as liquid paraffin; stearyl ethoxyl alcohol, esters of glycerol, isopropyl myristate, isotridecyl myristate, ethyl laurate, N-methylpyrrolidone, ethyl oleate, oleic acid, isopropyl adipate, isopropyl palmitate, octyl palmitate, 1,3-butanediol and mixtures thereof.

In another aspect, the present invention relates to the bandage of the invention for use for treating and/or accelerating healing of any skin defect, for example a wound, a burn or an ulcer. The invention finally relates to a method for tending to, and/or regenerating skin and/or accelerating healing of any skin defect, for example a wound, a burn or an ulcer comprising the local application of the bandage of the invention to said skin defect.

In a final aspect, the invention also relates to the cosmetic use of the composition of the invention in a bandage inducing healing without scarring. This use differs from the therapeutic application mentioned above in that it erases the traces of the wound once the wound is reclosed.

EXAMPLES

I. Equipment and Methods

I.1. Preparation of the Sample of Foetal Skin

The selection work of donors is ensured by the gynaecology-obstetrics service of the Nantes CHU. It consists of using foetuses of gestational age between 12 and 22 weeks retrieved during medical interruptions to pregnancy. These foetuses must have no anomaly linked to a virus or chromosome anomaly. The serology of the mother must be negative for: hepatitis C, AgHBs, Ac HBc, HIV 1 and 2, Ag p24, HTLV 1 and 2, CMV.

The foetuses are recovered during medical interruptions to pregnancy under echographic control, in sterile conditions. The obstetrician examines the foetus to look for malformations which would disqualify it.

The skin sample is taken in a delivery room by the senior obstetrician who places the sample in an empty sterile tube. The sample is covered by culture medium (DMEM/SVF) containing antibiotics (Penicillin-Streptomycin).

The sample of foetal skin is treated in an airflow cabinet in a controlled atmosphere zone of the UTCG. The skin sample is rinsed by immersion for 1 minute in 2 successive 50-ml tubes containing 20 ml DPBS/P-S (2%), then stirring. It is then transferred to a sterile tray and spread out with dermis on top.

The skin, held by means of forceps, is surface-scraped by a scalpel blade to take off the hypodermis. The blade of the scalpel is inclined at an angle of 45° relative to the surface of the skin. The skin is again rinsed by immersion and stirring in 2 successive 50-ml tubes containing 20 ml DPBS/P-S (2%).

The sample of foetal skin is placed in a Petri dish, epidermis facing up. Two fragments of 2 to 3 mm per side are cut out from the skin and are placed in a cryotube then dry-frozen at −80° C. These fragments are intended for additional research for theracanic purposes.

The rest of the skin is cut out in the smallest possible explants (around 1 mm per side).

The explants are then placed in 6-well plaques, at a rate of 10 explants per well, spaced uniformly. After 10 minutes dwell time, the explants are covered with 750 µl culture medium (DMEM complemented by 20% SVF, 1% P-S). The 6-well plaques are then placed in the incubator for 6 h or overnight. After this period, 2 ml of culture medium are added to each well. The 6-well plaques are transferred to the incubator at 37° C. in humid atmosphere with 5% $CO_2$ for 10 to 15 days on average.

Every 3 to 4 days, microscopic observation of the culture to evaluate the emergence of cells is performed. A change in medium is done by taking off half the medium and adding the equivalent of fresh medium DMEM/SVF (10%)/PS (1%).

After 10 to 15 days on average, the explants are enclosed by a crown of keratinocytes beyond which are the fibroblast mats. The fibroblasts and keratinocytes are recovered separately, twice.

I.2. Production of Foetal Fibroblasts

Initial trypsination produces fibroblasts. For this, the culture medium is taken off the 6-well plaques using a pipette. The wells are then rinsed with 2 ml DPBS.

DPBS is taken off each well and replaced by 0.5 ml of trypsin-EDTA 1×. The plaques are incubated at 37° C. for 5 to 10 min. Trypsin is used at ambient temperature to allow the keratinocytes remain adherent while the fibroblasts detach. The delamination is verified by observation of plaques by microscope.

The fibroblasts are taken up with 1 ml of DMEM/SVF (10%)/PS (1%) per well to inhibit the action of the trypsin. The fibroblasts in suspension are "pooled" in a 15- or 50-ml tube which will be centrifuged. The supernatant is eliminated and the PRBC cellular is taken up in 1 to 5 ml of DMEM/SVF medium (10%)/PS (1%). The fibroblasts are seeded at the rate of 8000 to 12000 cells per $cm^2$ in culture flasks which are transferred to the incubator at 37° C./5% $CO_2$ for 7 to 10 days.

Every 3 to 4 days, microscopic observation of the culture to evaluate the emergence of cells is performed. A change in medium is made by taking off half of the medium and adding the equivalent of fresh medium DMEM/SVF (10%)/PS (1%).

Figure 4:
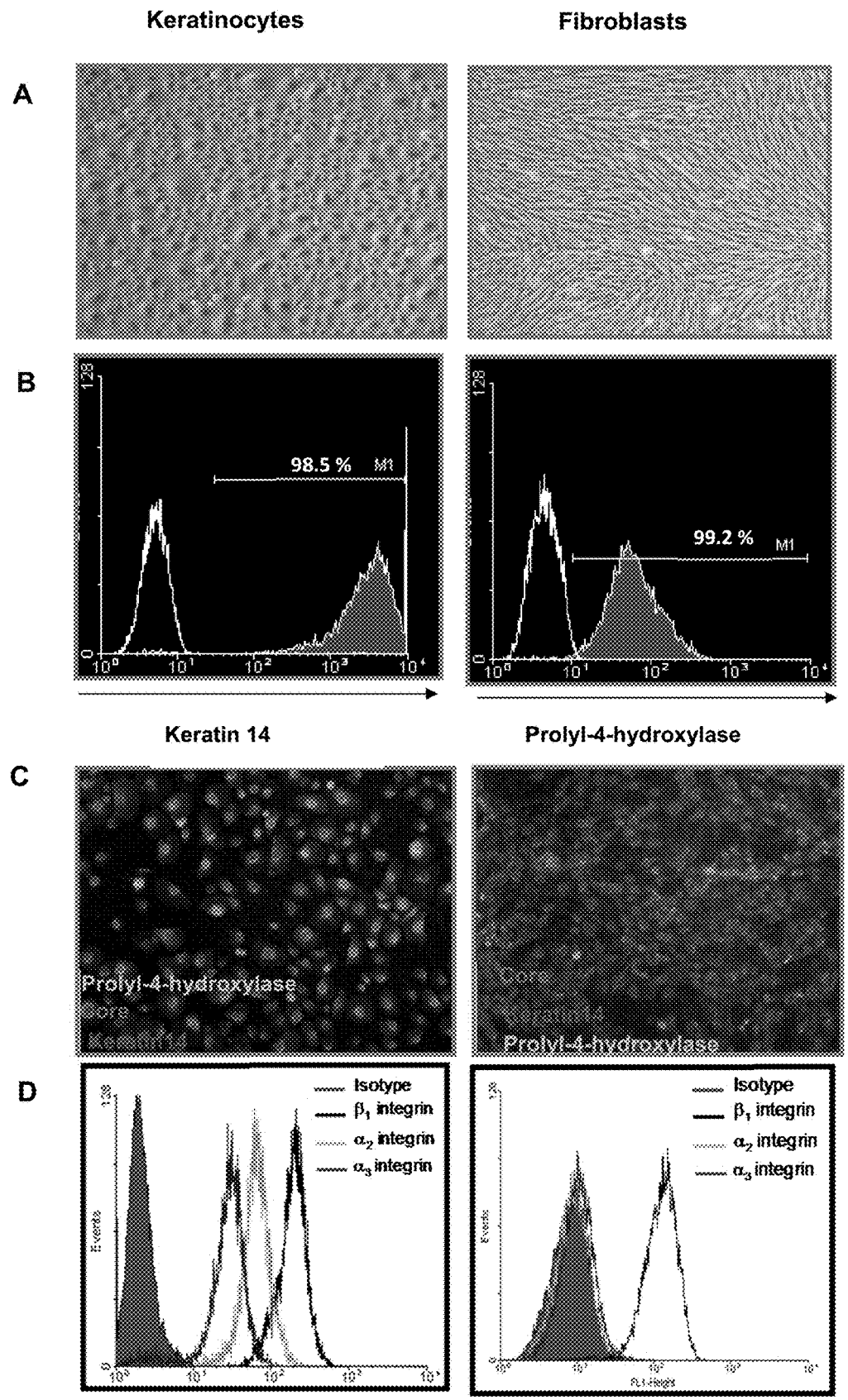

Samples are frozen at this stage to form an initial bank of foetal fibroblast cells on completion of first pass (P1). For freezing, the cells are adjusted to 1 million cells per ml in a freezing solution comprising human albumin at 4% and dymethyl sulfoxide (DMSO) at a 9:1 ratio. The cells are aliquoted in 2-ml cryotubes at the rate of 1 ml per tube. The freezing of these cryotubes is done by dropping the temperature from 1° C./minutes to −80° C. then after 24 to 72 hours the cryotubes are transferred in nitrogen vapour between −130 and −196° C. An aliquot of the initial bank is then thawed, then the foetal fibroblast cells are amplified for 2 more passes in DMEM/SVF medium (10%) and frozen following the procedure described hereinabove to constitute a clinical batch (work bank) of foetal fibroblast cells at P3. The morphological aspect and the expression of prolyl-4-hydroxylase and integrins ß1, α2 and α3 are controlled by conventional microscopy, FACS and immunofluorescence (FIG. 4).

I.3. Production of Foetal Keratinocytes

When the fibroblasts are recovered after trypsination, the 6-well plaques are rinsed with 2 mL DPBS per well and the initial culture medium is replaced by CnT-07/PS medium (1%) to benefit proliferation of keratinocytes. The plaques are incubated for 3 to 7 days at 37° C./5% $CO_2$.

Every 3 to 4 days, the culture is observed by microscope to evaluate the emergence of cells. A change in medium is made by taking off half of the medium and adding the equivalent of fresh CnT-07/PS medium (1%).

Where the number of cells allows it (confluence 70-80%), the keratinocytes are unstuck and put into culture. The culture medium is taken off the 6-well plaques using a pipette. The wells are then rinsed with 2 mL DPBS. The DPBS is taken off each well and replaced by 0.5 mL trypsin-EDTA 1×. The 6-well plaques are incubated at 37° C. for 10 to 15 minutes. The delamination is verified by observation of the plaques via microscope.

The keratinocytes are taken up with 1 ml DMEM/SVF (10%)/PS (1%) per well to inhibit the action of the trypsin. The keratinocytes in suspension are "pooled" in a 15- or 50-mL tube which will be centrifuged. The supernatant is eliminated and the PRBC is taken up in 1 to 5 ml of specific medium of keratinocytes, CnT-07.

A sampling for numbering/viability is made.

The keratinocytes are seeded at the rate of 4000 to 6000 cells per $cm^2$ in culture flasks.

The culture flasks are transferred to the incubator at 37° C./5% $CO_2$ for 7 to 10 days.

Samples are frozen at this stage to form an initial bank of foetal keratinocyte cells on completion of first pass (P1). For freezing, the cells are adjusted to 1 million cells per ml in the freezing solution comprising human albumin at 4% and dymethyl sulfoxide (DMSO) at a 9:1 ratio. The cells are aliquoted in 2-ml cryotubes at the rate of 1 ml per tube. The freezing of these cryotubes is carried out by dropping the temperature from 1° C./minutes to −80° C. then after 24 to 72 hours the cryotubes are transferred in nitrogen vapour between −130 and −196° C. An aliquot of the initial bank is then thawed, then the foetal keratinocyte cells are amplified for two more passes in CnT-07 medium and frozen as per the procedure described hereinabove to constitute a clinical batch (work bank) of foetal keratinocyte cells at P3. The morphological aspect and expression of the keratin 14 and integrins ß1, α2 and α3 are controlled by conventional microscopy, FACS and immunofluorescence (FIG. 4).

I.4. Profile of Cytokine Secretion of Two Cellular Types Obtained

The culture supernatants of keratinocytes, fibroblasts or mixture of both cellular types in different ratios coming from cultures of foetal type obtained hereinabove, or adult cells, were frozen after 48 hours culture and their VEGF-A, PDGF-AA, IL1β, GM-CSF, IL-1α, IL-8 and HGF content was analysed by ELISA dosage.

I.5. Immunomodulator Ability of Fibroblasts and Foetal Keratinocytes

Fibroblast cells and foetal keratinocyte obtained as described hereinabove were irradiated then put into presence of PBMC stimulated by phytohematogglutinin-L (PHA-L) and Interleukine 2 (IL-2). Different ratios of foetal cells/PBMC were tested (1/4; 1/20; 1/100; 1/200) to observe any effect of dose of foetal cells on lymphocyte proliferation. The proliferation was evaluated by incorporation of thymidin titrated after 5 days of culture.

I.6. Role of IDO (Indoleamine,2-3, Dioxygenase) on the Immunomodulator Ability of Fibroblasts and Foetal Keratinocytes.

The same type of experiment as that described in paragraph 1.5 was conducted, with the difference that to evaluate the role of the IDO on the immunomodulator ability of the fibroblasts and foetal keratinocytes the specific inhibitor of the IDO, 1-MT (1-methyl tryptophan) was added at concentrations of 200 µM, 20 µM and 2 µM during the lymphocyte proliferation phase so as to observe any reversal of the inhibitor effect of foetal cells on lymphocyte proliferation.

I.7. In-Vitro Healing Test of Foetal Cells

Figure 8:
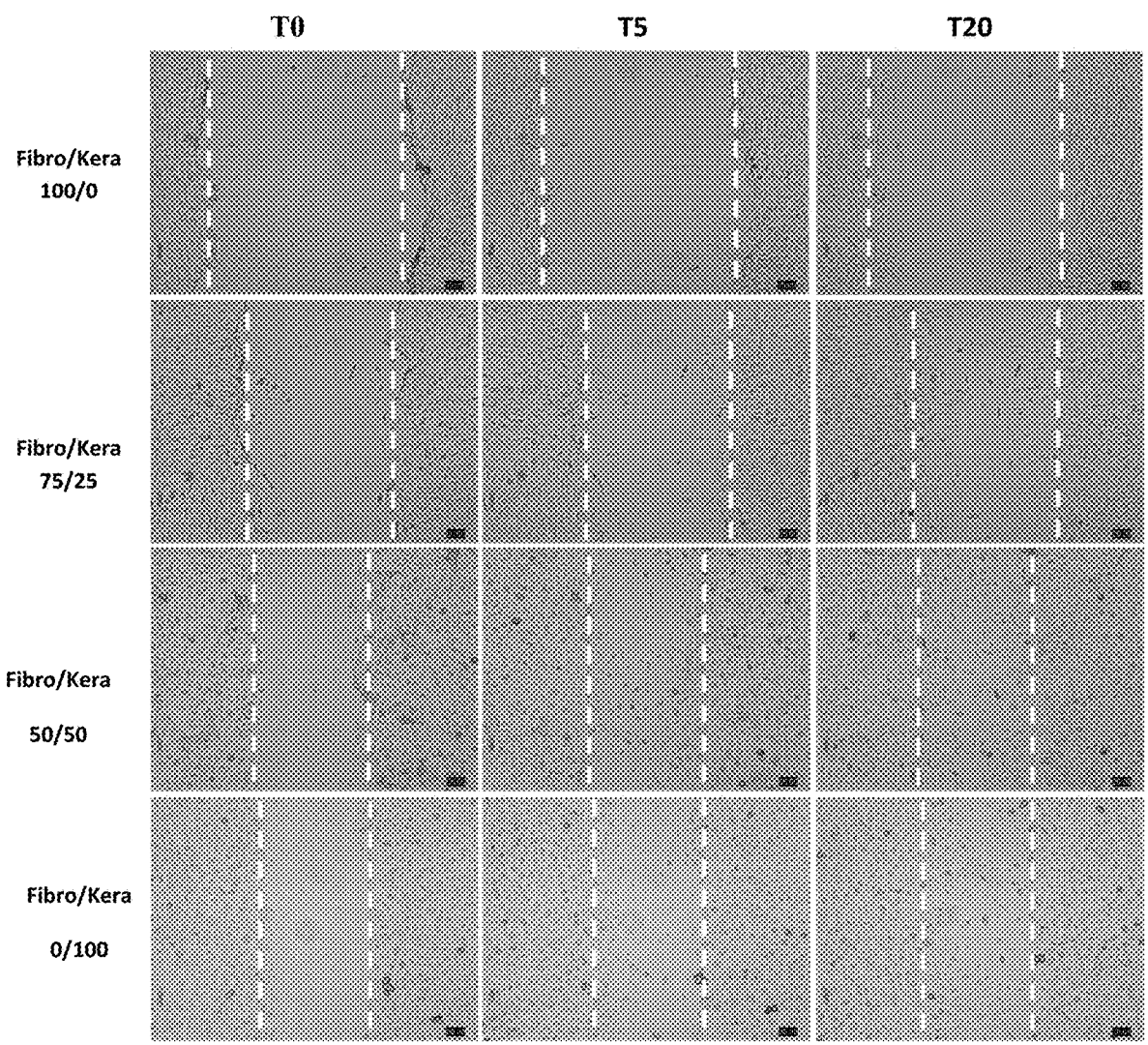
FIG. 8 illustrates images of the scratch obtained by microscopy at different times (TO, T5 and T20 hours) for different cellular conditions (ratio of fibroblasts/keratinocytes of 100/0, 75/25, 50/50 or 0/100).

This test was conducted from fibroblasts and keratinocytes obtained according to the protocols mentioned hereinabove. The aim of this test was to determine the ratio of each cellular type to obtain optimal healing. The cells were seeded in CnT-07 medium at a density close to confluence (100,000 cells per well of a 12-well plaque). After 24 h of additional culture, the cellular mat was "scratched" using a point (the measured width of the "scratch" is of the order of 300 to 500 µm, see FIG. 8). The cells were washed with PBS then non-complemented fresh medium was added to each well. The plaque was immediately analysed in time-lapse (real-time analysis of cells) over 23 hours.

For time-lapse analysis 4 points of each "scratch" were studied. For each of the points a photo was taken every 10 minutes over the 23 hours of analysis.

Different conditions were studied, corresponding to 4 different cellular mats:
1—Fibroblasts only (ratio fibro/kera 100/0)
2—75% Fibroblasts+25% keratinocytes (ratio fibro/kera 75/25)
3—50% Fibroblasts+50% keratinocytes (ratio fibro/kera 50/50)
4—keratinocytes only (ratio fibro/kera 0/100).

Analysis of the results was made using the imaging software Image J®. Measuring the closing of the scratch was evaluated by the percentage of cellular coverage of the scratched zone at times of temps TO, 5 h, 10 h, 15 h and 20 h. This coverage percentage was compared to the average cellular coverage of zones to right and left of the scratch (zones of cellular mat) considered as 100% of cellular coverage.

II—Results

II.1. Secretion of Cytokines by the Fibroblast Cells and Foetal Keratinocyte Only or Mixed (Ratio 1:1)

The results are presented in FIG. 1.

The foetal cells, and more particularly the foetal fibroblasts, strongly secrete VEGF-A. During co-culture of fibroblasts and foetal keratinocytes, the fact of obtaining VEGF-A concentration of the same value as that obtained in the case of culture of fibroblasts indicates only that there is potentialisation of VEGF-A secretion between the two cellular types. In fact, if this were not the case, the VEGF concentration would be lower in the supernatant of the co-culture relative to that of fibroblasts only, the secretion level of the keratinocytes being lower.

The PDGF-AA and IL-1 ß factors are specifically secreted by the foetal keratinocytes. When the fibroblasts and the foetal keratinocytes are mixed at a 1:1 ratio, secretion of these two factors is always evident even though the latter is lower than for keratinocytes only.

These dosages show that each cellular type secrets growth factors very differently qualitatively and quantitatively. Also, these results show that the association of keratinocytes and fibroblasts (at least at a 1:1 ratio) do not prevent release of factors specific to each of the two cellular types but on the contrary, for some factors, this release can be potentialised (for VEGF-A especially).

II.2. Comparison of the Cytokine Profile of Fibroblast Cells and Foetal and Adult Keratinocyte, Only or Mixed (Ratio 1:1)

Figure 2:
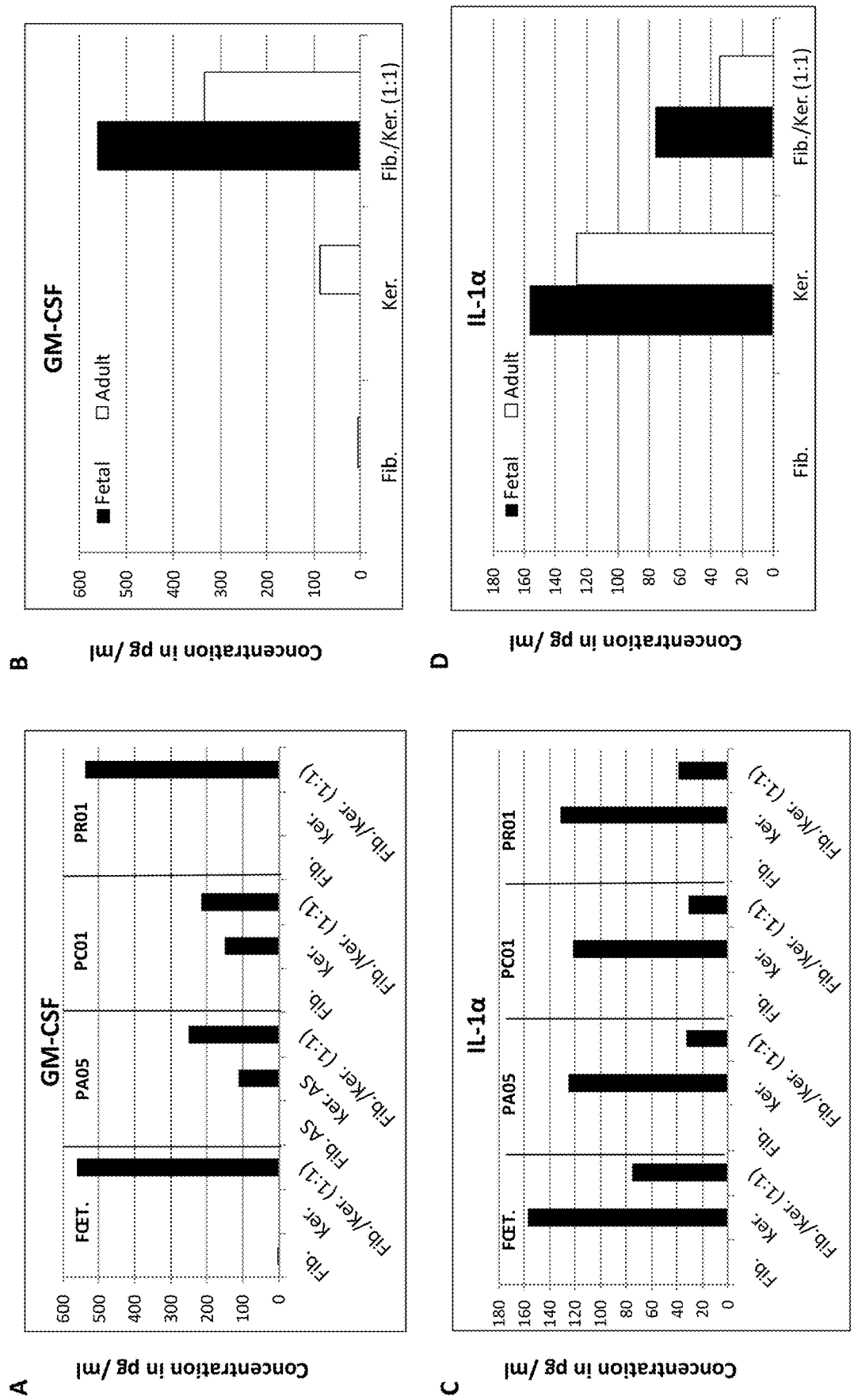

The results are presented in FIG. 2.

GM-CSF (FIGS. 2A and 2B)

The Inventors observed that fibroblasts and foetal keratinocytes only do not secrete GM-CSF. However, when these cells are co-cultivated at a 1:1 ratio, GM-CSF is strongly over-expressed in the culture supernatant (562 pg/ml).

Also, irrespective of the source of samples of adult fibroblasts used, these secrete no GM-CSF. The adult keratinocytes of the PA01 (abdominoplasty) and PC01 (thigh plasty) samples per se secrete a small quantity of GM-CSF (110 and 150 pg/ml).

The PR01 (foreskin) sample presents a secretion profile of GM-CSF close to that of foetal cells since each cellular type alone secretes no GM-CSF, but potentialisation of the secretion of this cytokine is observed in co-culture (538 pg/ml).

These results clearly show that the association of fibroblasts and foetal keratinocytes potentialises secretion of GM-CSF, more so than with co-culture of adult cells (562 vs 335 pg/ml).

IL-1α (FIGS. 2C and 2D)

The Inventors observed very similar secretion profiles of IL-1α, irrespective of the cellular samples tested. In this way, it seems that fibroblasts secrete no IL-1α in monoculture, whereas keratinocytes do secrete (up to 157 pg/ml for cells of foetal type).

When fibroblasts and keratinocytes are in co-culture at a 1:1 ratio, a decrease in secretion of IL-1α is observed. This decrease however is much greater in adult cells than in cells of foetal type.

IL-8 (FIGS. 2E and 2F)

The secretion profiles of IL-8 are also very similar. So, it appears that the fibroblasts and the foetal keratinocytes do not secrete in monoculture. Only adult keratinocytes originating from the PA05 (abdominoplasty) and PC01 (thigh surgery) samples secrete at very low levels (respectively 870 and 1000 pg/ml).

But co-culture of keratinocytes and fibroblasts considerably boost IL-8 secretion, both for foetal cells (6632 pg/ml) and for adult cells (5590 pg/ml).

HGF (FIGS. 2G and 2H)

In monoculture, neither fibroblasts nor foetal keratinocytes secrete HGF. However, a considerable rise in concentration of HGF is observed in co-culture (39.5 pg/ml). The comparison of foetal and adult cells in co-culture shows that foetal cells secrete HGF factor more strongly than adult cells (39.5 vs 23 pg/ml). Also, it seems that the association of fibroblasts and foetal keratinocytes substantially potentialises HGF secretion, whereas the inverse effect is observed with adult cells.

VEGF-A (FIGS. 2I and 2J)

The Inventors observed that foetal fibroblasts secrete twice as much VEGF-A as fibroblasts of adult donors (2770 vs 1323 pg/ml). However, VEGF-A secretion by adult keratinocytes is higher than with foetal keratinocytes (1875 vs 1404 pg/ml).

Also, foetal fibroblasts secrete more VEGF-A than foetal keratinocytes (2770 vs 1404 pg/ml), and inversely for adult cells (1875 pg/ml in keratinocytes vs 1323 pg/ml in fibroblasts).

Finally, in co-culture, foetal cells secrete slightly more VEGF-A than adult cells (2617 vs 2100 pg/ml).

Conclusion

In this way, the Inventors have demonstrated that co-culture of fibroblasts and foetal keratinocytes is essential for secretion of GM-CSF, IL-8 and HGF factors, which are not naturally secreted by these cells in monoculture. This co-culture also positively influences VEGF-A secretion, even moderately.

The present results also show that, in co-culture conditions (ratio 1:1), secretion of GM-CSF, HGF, 11-8, IL-1α and VEGF-A factors is higher with fibroblasts and keratinocytes of foetal origin than with adult cells.

II.3. Cytokine Profile of Fibroblast Cells and Foetal Keratinocyte at Different Ratios To study the influence of the ratio of fibroblast cells and foetal keratinocyte on cytokine production the Inventors studied the concentration of different cytokines as a function of different ratios of these cells.

Figure 3:
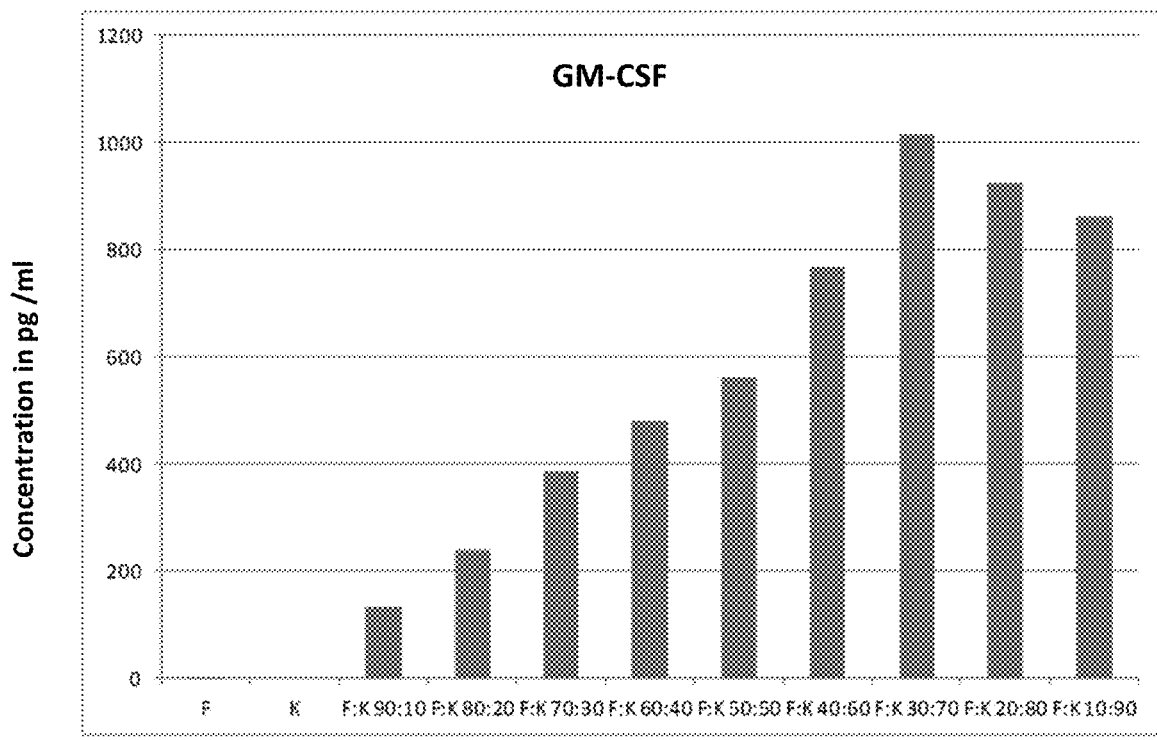
Figure 3:
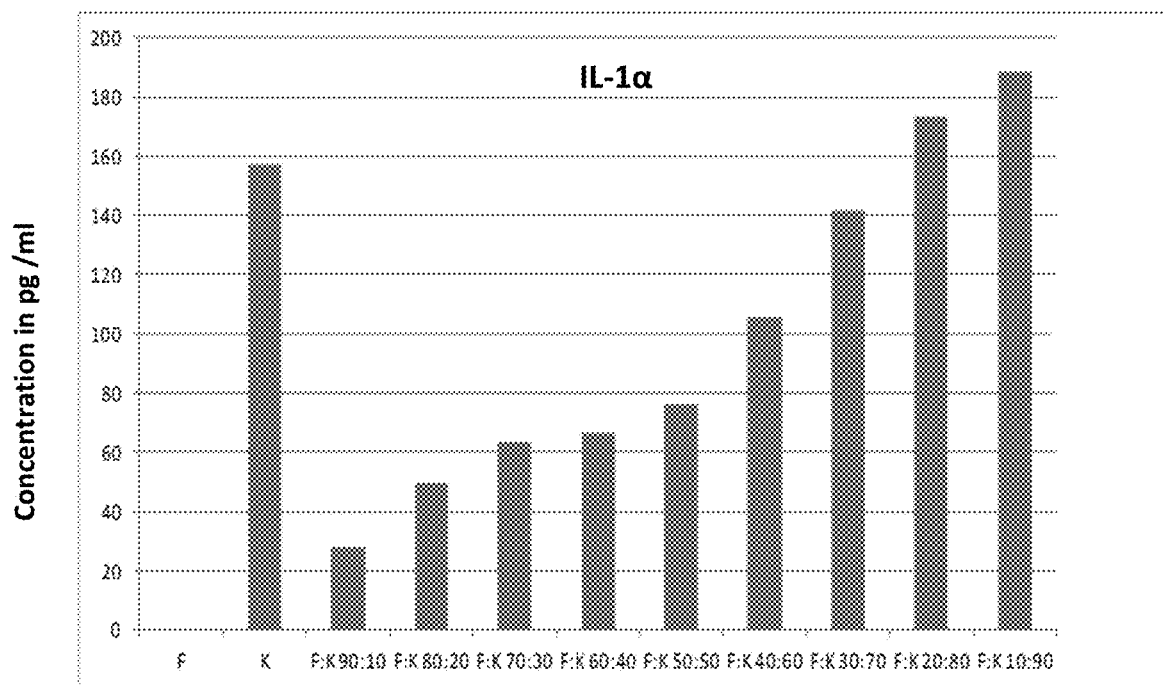

The results of this study are presented in FIG. 3.

GM-CSF (FIG. 3A)

The Inventors observed that it is the association of fibroblasts and foetal keratinocytes which allows said cells to express GM-CSF. Accordingly, these results confirm that the interactions between these two cellular types are necessary for secretion of GM-CSF.

In addition, the more the proportion of keratinocytes increases, the more the secretion of GM-CSF increases, until it reaches a plateau at a ratio of 30% fibroblasts/70% keratinocytes (1014 pg/ml). GM-CSF secretion then starts to drop when the keratinocyte proportion exceeds 70%.

IL-1α(FIG. 3B)

As per the results of point 11.2, it is evident that only foetal keratinocytes secrete IL-1α. However, in contrast to GM-CSF, co-culture of fibroblasts and foetal keratinocytes seems not to influence IL-1α secretion. So, at a ratio of 90% fibroblasts/10% keratinocytes IL-1 α secretion is very low and increases progressively to the inverse ratio (10% fibroblasts/90% keratinocytes) reaching a level slightly above that obtained for keratinocyte monoculture (188 pg/ml vs. 157 pg/ml). A ratio of 50% of each cellular type reaches half the level obtained for monoculture of keratinocytes.

IL-8 (FIG. 3C)

As for GM-CSF, the Inventors observed that it is the association of fibroblasts and foetal keratinocytes which causes IL-8 expression. In this way, these results confirm that the interactions between these two cellular types are necessary for secretion of this cytokine.

The maximal level of IL-8 secretion is attained for the ratio 70% fibroblasts/30% keratinocytes (5470 pg/ml) but this does remain relatively stable up to a 50%/50% ratio (4464 pg/ml). Then, the more the keratinocyte proportion increases (above 50%), the more the secretion of IL-8 decreases.

HGF (FIG. 3D)

As for GM-CSF and IL-8, the association of fibroblasts and foetal keratinocytes allows said cells to secrete HGF. So these results confirm that interactions between these two cellular types are necessary for expression of HGF.

However, the ratio between fibroblasts and foetal keratinocytes seems not to influence the level of HGF secretion (which varies between 21 and 25 pg/ml).

VEGF-A (FIG. 3D)

As observes in point 11.2, VEGF-A is the only cytokine expressed by fibroblasts and foetal keratinocytes in monoculture.

Combining these two cellular types positively influences the expression of VEGF-A. So a maximal concentration of VEGF-A is observed for the ratio 90% fibroblasts/10% keratinocytes (3570 pg/ml). Next, the more the proportion of keratinocytes increases, the more the concentration of VEGF-A decreases.

Conclusion

These results confirm that combining fibroblasts and foetal keratinocytes enables the over-expression of several growth factors and cytokines, and in particular GM-CSF, HGF and IL8 which are not naturally expressed in these cells in monoculture and which are known for their implication in the healing process.

The ratio between these two cellular types also modulates secretion of these factors and cytokines. The results show especially that the release of these factors is generally lower with a fibroblast/keratinocyte ratio of 9:1 (WO 03/068287, Neocutis SA), relative to a ratio of 1:1. The IL-1α concentration, which is known for its role in healing, is especially higher when the proportion of keratinocytes increases.

It also appears that a ratio of fibroblasts/keratinocytes of 3:7 seems to be optimal since it produces maximal expression of HGF and GM-CSF and maintains optimal expression of IL-1α, which is essential for healing. Even though the levels of VEGF-A and IL-8 expression are not optimal at this ratio, they do remain relatively considerable. In this respect, it should be noted that apart from a pro-healing function, cytokine IL-8 exhibits pro-inflammatory properties. Accordingly, excessive concentration of IL-8 is not preferable because the latter could result in increase of the inflammatory response which would be harmful for quality of healing.

II.2. Characterisation of Fibroblast Cells and Foetal Keratinocytes

The results are presented in FIG. 4.

They show that the cells coming from clinical batches of keratinocytes and fibroblasts have a morphology characteristic of keratinocytes and fibroblasts respectively. The purity of these clinical batches was validated by cytometry. Therefore, 98.5% of cells of the clinical batch of keratinocytes express the keratin 14 (specific marker of keratinocytes) and 99.2% of cells coming from the clinical batch of fibroblasts express prolyl-4-hydroxilase (fibroblast marker). These results validate the selected production process which produces two banks of very pure keratinocytes and fibroblasts from a single sample of foetal skin.

II.3. Inhibition of the Lymphoproliferation by the Fibroblast Cells and Foetal Keratinocyte in Mixture The results are presented in FIG. 5.

These results show that there is inhibition of lymphocyte proliferation caused by the fibroblasts and foetal keratinocytes. This inhibition seems to be dose-dependent and above all it is always effective when fibroblasts and keratinocytes are mixed in the same ratio.

These results show that it is advantageous to use foetal cells in an allogenic system since they are capable of inhibiting lymphocyte activation. So by blocking lymphocyte activation of the host, the foetal cells not only will be well tolerated and could therefore play their accelerator role of healing by their paracrine activity. Likewise, their immunosuppressive properties will be reflected locally by a decrease in inflammation and therefore improvement in the quality and of the aesthetic aspect of the scar (which depends on the degree of inflammation).

II.4. IDO is Responsible for the Inhibitor Effect of Foetal Cells on Lymphocyte Proliferation The results are presented in the graphics a, b and c of FIG. 5B.

These results show that the foetal cells of the invention (fibroblasts, keratinocytes or fibroblasts+keratinocytes) inhibit lymphocyte proliferation, in the absence of 1-MT. In all cases (fibroblasts, keratinocytes or fibroblasts+keratinocytes), adding 1-MT to 200 µM heightens inhibition of proliferation such that in the presence of the inhibitor at this concentration lymphocyte proliferation returns almost to the same level as that of the positive control (lymphocytes+PHA-L+IL-2). Also, it is evident that the effect of 1-MT is dose-dependent.

These results show that inhibition of lymphocyte proliferation by the fibroblast cells and foetal keratinocyte of the invention are based on the enzyme activity of IDO, which is well known for this type of cell.

II.5. Evolution of the Closing of the Scratch Over Time

Figure 6:
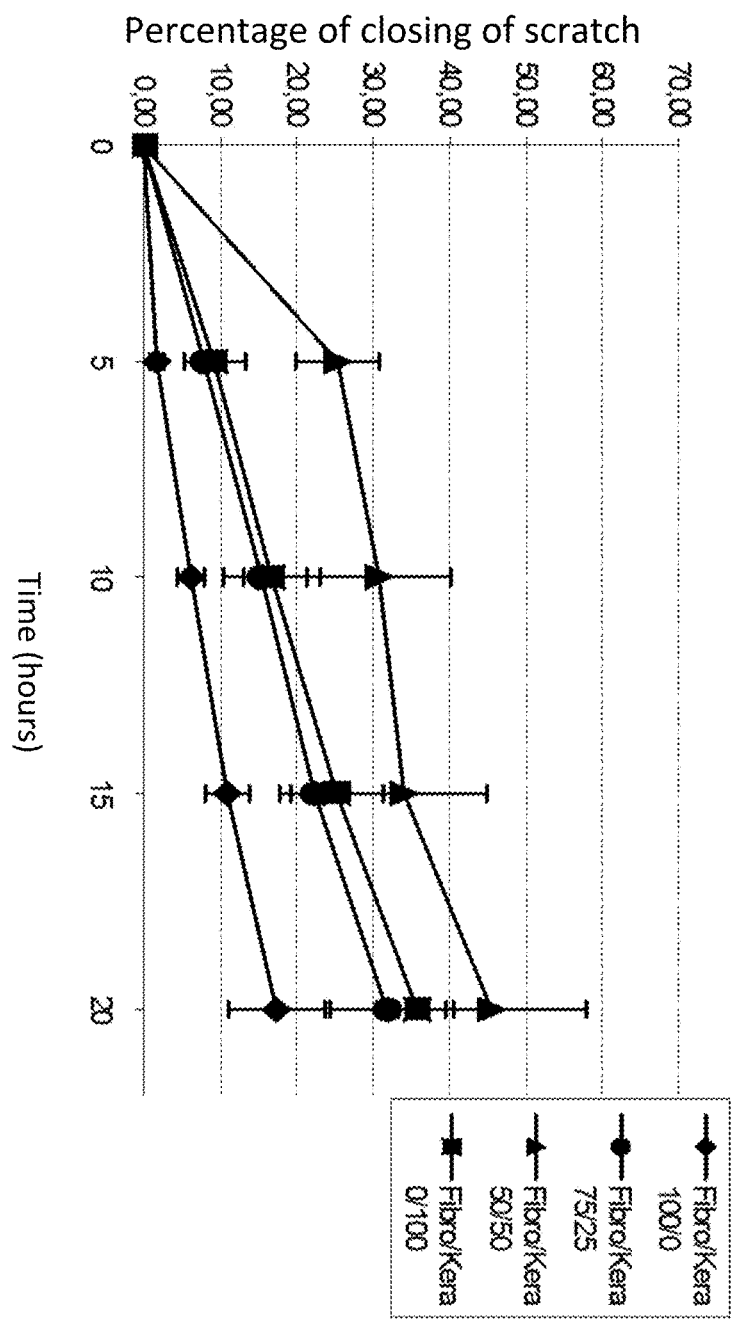
FIG. 6 illustrates the evolution of the closing of a cellular scratch over time (between 0 and 20 hours after the scratch), for different cellular conditions (ratio of fibroblasts/keratinocytes of 100/0, 75/25, 50/50 or 0/100).

The results are presented in the graphic of FIG. 6.

These results show:
1—Very fast closing of the scratch from the outset in the condition of Fibroblasts 50%/keratinocytes 50%. Then stabilisation by 15 h then again strong acceleration of the coverage of the scratch zone.

2—In the condition of 100% fibroblasts, initial closing is very slow then increases after 5 h but closing of the scratch remains relatively moderate to reach only 17% at 20 h.

3—For the conditions of 100% keratinocytes and 75% fibroblasts/25% keratinocytes closing of the scratch is done in linear manner, from the outset up to 20 hours to reach around 35% closing on completion of acquisition.

II.6. Closing of the Scratch at Times of 5 h and 20 h as a Function of Conditions.

Figure 7:
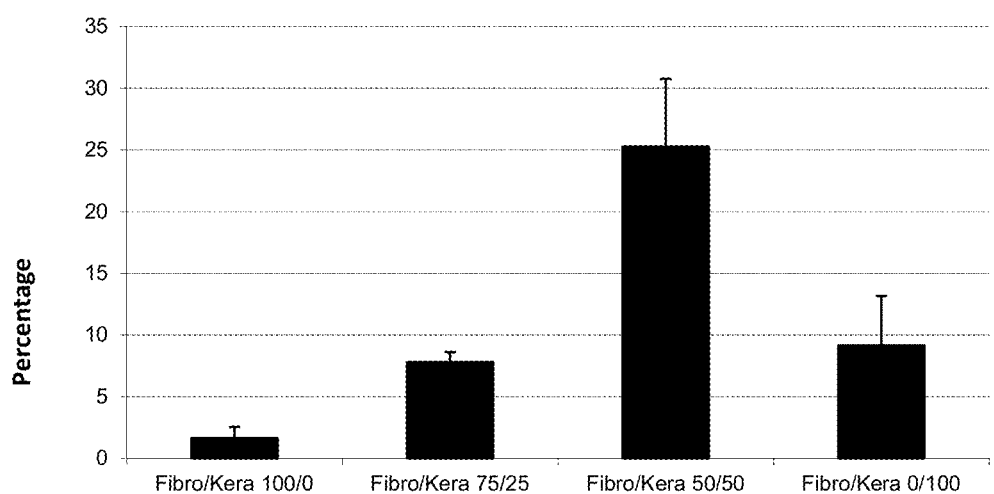
FIG. 7 illustrates the closing percentage of the scratch at 5 hours (FIG. 7A) or 20 hours (FIG. 7B) after the latter has been performed, for different cellular conditions (ratio of fibroblasts/keratinocytes of 100/0, 75/25, 50/50 or 0/100).
Figure 7:
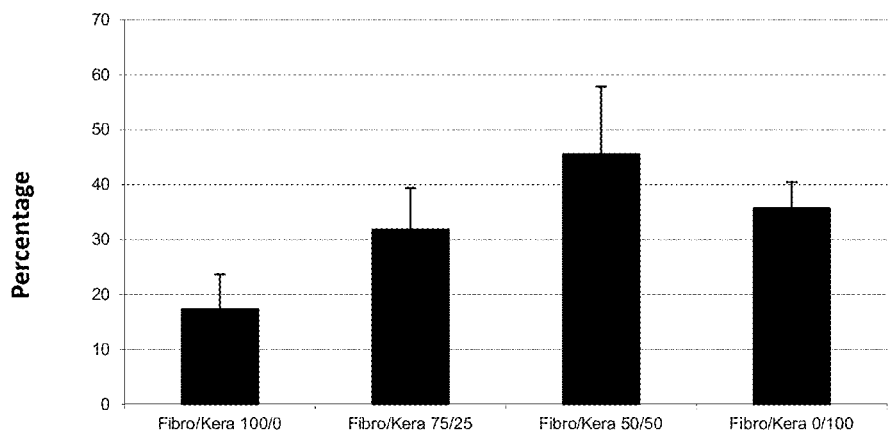

The results are presented in FIGS. 7A and 7B. This other representation of results reveals the importance of the keratinocytes/fibroblasts ratio between the different conditions at the earliest time and on completion of acquisition.

Via this in-vitro healing test it appears that combining fibroblasts and keratinocytes at a highly precise ratio of 50%/50% enables faster closing of the scratch zone relative to the use of fibroblasts or keratinocytes alone. This ratio seems particularly efficacious during initial closing of the scratch zone.

III— Examples of Skin Substitutes According to the Invention

III.1 Preparation of a Skin Substitute Based on Tissucol® According to the Invention Fibroblast and foetal keratinocyte cells preserved in liquid nitrogen as per the protocol described hereinabove were been thawed, seeded in a 75-cm$^2$ culture flask and incubated at 37° C. in humid atmosphere with 5% $CO_2$ over 48 hours. The fibroblast and keratinocyte cells were treated separately in trypsin/EDTA 1× until complete delamination of the culture flask. DMEM medium complemented by 10% SVF was added to inhibit the action of the trypsin. The keratinocyte and fibroblast cells were centrifuged then counted (always separately). An equal number of fibroblast and keratinocyte cells (ratio of keratinocytes:fibroblasts=1:1), from 0.2 0 0.10$^6$ cells to 10×10$^6$, preferably 2.10$^6$, was thoroughly mixed in the same 15-ml tube. This tube was centrifuged and the PRBC taken up in a volume of 1 mL of the second component of the kit (human thrombin+calcium chloride). The first component of the Tissucol® (human fibrinogen+factor III of human coagulation+human fibronectin+human plasminogen+bovine aprotinin) was mixed at equal volume with the second component of the biological adhesive due to the use of the 1-mL Tissucol® kit. The two mixed components of the adhesive can be placed on a wound, a burn or an ulcer.

III.2 Preparation of a Skin Substitute Based on Bovine Collagen I According to the Invention III.2.a) Fibroblast and foetal keratinocyte cells preserved in liquid nitrogen as per the protocol described hereinabove were thawed, seeded in a 75-cm$^2$ culture flask and incubated at 37° C. in humid atmosphere with 5% $CO_2$ over 48 hours. The fibroblast and keratinocyte cells were then treated separately in trypsin/EDTA 1× until complete delamination of the culture flask. DMEM medium complemented by 10% SVF was added to inhibit the action of the trypsin. The keratinocyte and fibroblast cells were then centrifuged then counted (always separately). An equal number of fibroblast and keratinocyte cells (ratio keratinocytes:fibroblasts=1:1) was then transferred to a 15-ml tube, centrifuged and taken up in the DMEM culture medium complemented by 10% SVF. The fibroblast and keratinocyte cells mixed at a 1:1 ratio were seeded on a spongy matrix of type-I bovine collagen at a density from 0.1×10$^6$ and 5×10$^6$ cells per cm$^3$ of matrix. The seeded cells on the matrix were incubated at 37° C. in humid atmosphere with 5% $CO_2$. After 48 hours, the cellularised matrix can be applied to the wound, burn or ulcer.

III.2.b) The protocol described in point III.2.a) hereinabove was then optimised as follows: fibroblast and foetal keratinocyte cells preserved in liquid nitrogen were thawed, then directly seeded on the matrix of bovine collagen I after thawing, without undergoing return to culture as per protocol III.2.a). The 1:1 ratio of keratinocytes:fibroblasts were also maintained. The seeded cells on the matrix were incubated at 37° C. in humid atmosphere with 5% $CO_2$. After 72 h hours, the cellularised matrix can be applied to the wound, burn or ulcer.

This protocol has several advantages relative to that disclosed in point III.2.a) hereinabove, since it:

(i) limits the number of interventions by operators, and simplifies preparation of the skin substitute; and (ii) gains 24 h over preparation time of the skin substitute, making it more quickly available for the patient.

Enzymatic dosages of LDH (lactate dehydrogenase) activity, released by the cells in the skin substitute, have also shown that this novel preparation mode enables excellent survival of cells. In particular, this optimised preparation process produces 85% of cellular viability in the bandage at the time of seeding, and 82% 3 days after seeding, on completion of preparation of the skin substitute.

BIBLIOGRAPHICAL REFERENCES

Begaud B. Epidemiology of leg ulcers. *Ann Dermatol Venereol* 2002: 129: 1225-1226

Bullard K M, Longaker Mont., Lorenz H P. Fetal wound healing: current biology. *World J Surg* 2003: 27: 54-61

Chester D L, Balderson D S, Papini R P G. A review of keratinocyte delivery to the wound bed. *J Burn Care Rehabil* 2004; 25: 266-275

Clark R A F, Lanigan J M, Della Pelle P, Manseau E, Dvorak H F, Colvin R B. Fibronectin and fibrin provide a provisional matrix for epidermal cell migration during wound reepithelialization. *J Invest Dermatol* 1982: 79: 264-269

Ho C, Tran K, Hux M, Campbell K. Grafts of artificial skin in the treatment of chronic wounds: meta-analysis of the clinical efficacy and cost-efficacy study. Technological report No. 52. Ottawa: Canadian Office for coordination of evaluation of health technologies 2005

Hohlfeld J, de Buys Roessingh A, Hirt-Burri et al. Tissue-engineered fetal skin constructs for paediatric burns. *Lancet* 2005: 366: 840-842

Hunyadi J, Farkas B, Bertenyi C, Olah J, Dobozy A. Keratinocyte grafting: a new means of transplantation for full-thickness wounds. *J Dermatol Surg Oncol* 1988:14 (1): 75-78

Jones J E, Nelson E A. Skin grafting for venous leg ulcers (review). The Cochrane library 2006: Issue 1

Rheinwald and Green. Serial cultivation of strains of human epidermal keratinocytes: the formation of keratinizing colonies from single cell. *Cell* 1975: 6: 331-344

Shen J T, Falanga V. Innovative therapies in wound healing. *J Cutan Med Surg* 2003: 217-224

The invention claimed is:

1. A composition for accelerating healing of a skin defect comprising a mixture of foetal human keratinocyte cells and foetal human fibroblastic cells in a skin healing accelerating ratio between said keratinocyte and fibroblast cells ranging from 1:1 to 2.5:1.

2. The composition according to claim 1, wherein said ratio is 1:1 or 7:3.

3. The composition according to claim 1, wherein said mixture of cells is integrated in a non-immunogenic extracellular matrix.

4. The composition according to claim 3, wherein said mixture of cells is present in a concentration consisting of between $0.1 \times 10^6$ and $5 \times 10^6$ cells per $cm^3$ of matrix.

5. The composition according to claim 3 wherein said matrix contains at least one compound selected from the group consisting of collagen, fibronectin, fibrin, and elastin, and mixtures thereof.

6. The composition according to claim 3, wherein said matrix is composed of human fibrinogen, human factor XIII, human fibronectin, plasminogen, bovine aprotinin and human thrombin.

7. A bandage containing a composition which comprises a mixture of foetal human keratinocyte cells and foetal human fibroblastic cells, the ratio between said keratinocyte and fibroblast cells ranging from 0.75 to 2.5.

8. The bandage according to claim 7, wherein said bandage is sterile and packaged in a container impermeable to microorganisms.

9. A method for treating a skin defect in a patient in need thereof, comprising the step of administering to said patient a composition which comprises a mixture of foetal human keratinocyte cells and foetal human fibroblastic cells, the ratio between said keratinocyte and fibroblast cells ranging from 0.75 to 2.5.

10. A process for manufacturing a composition comprising the step of mixing foetal human keratinocyte cells and foetal human fibroblastic cells with a non-immunogenic extracellular matrix, in a ratio ranging from 0.75 to 2.5.

11. The manufacturing process according to claim 10, wherein said ratio is 1:1 or 7:3.

12. The manufacturing process according to claim 10 comprising, prior to said mixing step, the following two steps:
a) obtaining foetal human keratinocyte cells, and
b) obtaining foetal human fibroblastic cells.

13. The manufacturing process according to claim 10 comprising, prior to the mixing step, the following two steps:
a) obtaining a bank of foetal human keratinocyte cells, and
b) obtaining a bank of foetal human fibroblastic cells.

14. The bandage according to claim 7 wherein said ratio is 1:1 or 7:3.

15. The method according to claim 9 wherein the skin defect is a wound, a burn or an ulcer.

16. The method according to claim 9 wherein said ratio is 1:1 or 7:3.

17. The composition according to claim 1, wherein the skin defect is a wound, a burn or an ulcer.

* * * * *